US009596444B2

(12) United States Patent
Tsukagoshi et al.

(10) Patent No.: US 9,596,444 B2
(45) Date of Patent: Mar. 14, 2017

(54) IMAGE PROCESSING SYSTEM, APPARATUS, AND METHOD

(75) Inventors: Shinsuke Tsukagoshi, Nasushiobara (JP); Yoshiyuki Kokojima, Yokohama (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 681 days.

(21) Appl. No.: 13/530,558

(22) Filed: Jun. 22, 2012

(65) Prior Publication Data

US 2012/0327198 A1 Dec. 27, 2012

(30) Foreign Application Priority Data

Jun. 22, 2011 (JP) ................................ 2011-138676

(51) Int. Cl.
*H04N 13/04* (2006.01)
*H04N 13/00* (2006.01)
*A61B 6/00* (2006.01)
*A61B 6/02* (2006.01)

(52) U.S. Cl.
CPC ......... *H04N 13/0011* (2013.01); *A61B 6/022* (2013.01); *A61B 6/466* (2013.01); *H04N 13/0438* (2013.01); *H04N 13/0022* (2013.01)

(58) Field of Classification Search
CPC ........... H04N 13/0022; H04N 13/0275; G02B 26/001
USPC ........................................................... 348/51
See application file for complete search history.

(56) References Cited

U.S. PATENT DOCUMENTS

| | | | |
|---|---|---|---|
| 7,605,776 B2 | 10/2009 | Satoh et al. | |
| 2002/0163482 A1 | 11/2002 | Sullivan | |
| 2004/0066555 A1* | 4/2004 | Nomura | 359/462 |
| 2004/0085310 A1 | 5/2004 | Snuffer | |

(Continued)

FOREIGN PATENT DOCUMENTS

| | | |
|---|---|---|
| CN | 1788497 A | 6/2006 |
| EP | 2 536 156 A2 | 12/2012 |

(Continued)

OTHER PUBLICATIONS

Extended European Search Report issued Jul. 2, 2014 in Patent Application No. 12173282.0.

(Continued)

*Primary Examiner* — Obafemi Sosanya
(74) *Attorney, Agent, or Firm* — Oblon, McClelland, Maier & Neustadt, L.L.P.

(57) ABSTRACT

An image processing system according to an embodiment includes a stereoscopic display device, a transform unit, an image generating unit, and a display control unit. The transform unit reduces or enlarges volume data which is three-dimensional (3D) image data such that among scales of a stereoscopic image assumed to be displayed on the stereoscopic display device using a parallax image group obtained from the volume data, a scale in a depth direction on a display surface of the stereoscopic display device is substantially the same as a scale in another direction which is a direction other than the depth direction. The image generating unit generates a parallax image group by performing a rendering process on transformed volume data. The display control unit causes the parallax image group to be displayed on the stereoscopic display device.

7 Claims, 20 Drawing Sheets

(56) References Cited

U.S. PATENT DOCUMENTS

2005/0253924 A1* 11/2005 Mashitani .......... H04N 13/0275 348/42
2007/0239489 A1* 10/2007 Masuzawa ............ G06F 19/321 705/3
2010/0179789 A1* 7/2010 Sachdeva ................. A61C 7/00 703/1
2011/0107270 A1* 5/2011 Wang .................. G06F 19/3437 715/850
2012/0313933 A1 12/2012 Tsukagoshi et al.
2014/0035914 A1 2/2014 Noshi et al.

FOREIGN PATENT DOCUMENTS

JP 2005-86414 3/2005
WO WO 2012/137732 A1 10/2012

OTHER PUBLICATIONS

Combined Chinese Office Action and Search Report issued Apr. 16, 2014 in Patent Application No. 201210210039.7 (with English translation of categories of cited documents).

* cited by examiner

IMAGE PROCESSING SYSTEM, APPARATUS, AND METHOD

CROSS-REFERENCE TO RELATED APPLICATIONS

This application is based upon and claims the benefit of priority from Japanese Patent Application No. 2011-138676, filed on Jun. 22, 2011; the entire contents of which are incorporated herein by reference.

FIELD

Embodiments described herein relate generally to an image processing system, apparatus, and method.

BACKGROUND

In the past, there has been known a technique of causing two parallax images, captured from two points of view, to be displayed on a monitor so that a user who uses a dedicated device such as stereoscopic view glasses can view a stereoscopic image. Further, in recent years, there has been developed a technique of causing multiple parallax images (for example, nine parallax images), captured from a plurality of points of view, to be displayed on a monitor using a light beam controller such as a lenticular lens so that the user can view a stereoscopic image with the naked eyes.

Further, among medical image diagnostic devices such as an X-ray Computed Tomography (CT) apparatus, a Magnetic Resonance Imaging (MRI) apparatus, or an ultrasonic diagnostic apparatus, there is an apparatus capable of generating a three-dimensional (3D) medical image data (hereinafter, referred to as "volume data"). Further, the medical image diagnostic device generates a planar image to display by executing a variety of image processing on volume data, and causes the planar image to be displayed on a general-purpose monitor. For example, the medical image diagnostic device generates a planar image on an arbitrary cross section in which 3D information on a subject is reflected by executing a volume rendering process on volume data, and causes the generated planar image to be displayed on a general-purpose monitor.

DETAILED DESCRIPTION

An image processing system according to an embodiment includes a stereoscopic display device, a transform unit, an image generating unit, and a display control unit. The stereoscopic display device displays a stereoscopically viewable stereoscopic image using a plurality of parallax images. The transform unit reduces or enlarges volume data which is three-dimensional (3D) image data such that among scales of a stereoscopic image assumed to be displayed on the stereoscopic display device using a parallax image group obtained from the volume data, a scale in a depth direction on a display surface of the stereoscopic display device is substantially the same as a scale in another direction which is a direction other than the depth direction. The image generating unit generates a parallax image group by performing a rendering process on transformed volume data transformed by the transform unit. The display control unit causes the parallax image group generated by the image generating unit to be displayed on the stereoscopic display device.

Hereinafter, embodiments of an image processing system, apparatus, and method will be described in detail with reference to the accompanying drawings. In the following, an image processing system including a workstation with a function as an image processing apparatus is described as an embodiment. Here, the terminology used in the following embodiments is described. A "parallax image group" refers to an image group which is generated by performing a volume rendering process on volume data while moving a point-of-view position by a predetermined parallactic angle at a time. In other words, the "parallax image group" is configured with a plurality of "parallax images" having different "point-of-view positions." Further, a "parallactic angle" refers to an angle determined by an adjacent point-of-view position among point-of-view positions set to generate the "parallax image group" and a predetermined position in a space (the center of a space) represented by volume data. Further, a "parallax number" refers to the number of "parallax images" necessary to implement a stereoscopic view by a stereoscopic display monitor. Further, a "nine-parallax image" described in the following refers to a "parallax image group" consisting of nine "parallax images." Furthermore, a "two-parallax image" described in the following refers to a "parallax image group" consisting of two "parallax images."

First Embodiment

Figure 1:
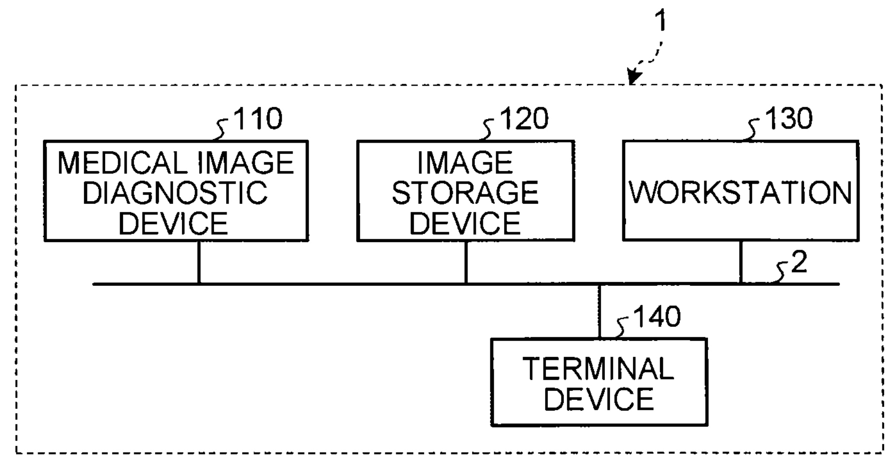
FIG. 1 is a diagram for describing a configuration example of an image processing system according to a first embodiment.

First, a configuration example of an image processing system according to a first embodiment will be described. FIG. 1 is a diagram for describing a configuration example of an image processing system according to the first embodiment.

As illustrated in FIG. 1, an image processing system 1 according to the first embodiment includes a medical image diagnostic device 110, an image storage device 120, a workstation 130, and a terminal device 140. The respective devices illustrated in FIG. 1 are connected to directly or indirectly communicate one another, for example, via a hospital Local Area Network (LAN) 2 installed in a hospital. For example, when a Picture Archiving and Communication System (PACS) is introduced into the image processing system 1, the respective devices exchange a medical image or the like with one another according to a Digital Imaging and Communications in Medicine (DICOM) standard.

The image processing system 1 provides an observer, who works in the hospital such as a doctor or a laboratory technician, with a stereoscopic image which is an image stereoscopically viewable to the observer by generating a parallax image group based on volume data which is 3D medical image data generated by the medical image diagnostic device 110 and then causing the parallax image group to be displayed on a monitor with a stereoscopic view function. Specifically, in the first embodiment, the workstation 130 performs a variety of image processing on volume data and generates a parallax image group. Each of the workstation 130 and the terminal device 140 includes a monitor with a stereoscopic view function, and displays a stereoscopic image to a user by displaying the parallax image group generated by the workstation 130 through the monitor. The image storage device 120 stores volume data generated by the medical image diagnostic device 110 and the parallax image group generated by the workstation 130. For example, the workstation 130 or the terminal device 140 acquires the volume data or the parallax image group from the image storage device 120, executes arbitrary image processing on the acquired volume data or the acquired parallax image group, and causes the parallax image group to be displayed on the monitor. The respective devices will be described below in order.

The medical image diagnostic device 110 is an X-ray diagnostic device, an X-ray Computed Tomography (CT) device, a Magnetic Resonance Imaging (MRI) device, an ultrasonic diagnostic device, a Single Photon Emission Computed Tomography (SPECT) device, a Positron Emission computed Tomography (PET) device, a SPECT-CT device in which a SPECT device is integrated with an X-ray CT device, a PET-CT device in which a PET device is integrated with an X-ray CT device, a device group thereof, or the like. The medical image diagnostic device 110 according to the first embodiment can generate 3D medical image data (volume data).

Specifically, the medical image diagnostic device 110 according to the first embodiment captures a subject, and generates volume data. For example, the medical image diagnostic device 110 generates volume data such that it collects data such as projection data or an MR signal by capturing a subject, and then reconstructs medical image data including a plurality of axial planes along a body axis direction of a subject based on the collected data. For example, when the medical image diagnostic device 110 reconstructs medical image data of 500 axial planes, a medical image data group of 500 axial planes is used as volume data. Alternatively, projection data or an MR signal of a subject captured by the medical image diagnostic device 110 may be used as volume data.

The medical image diagnostic device 110 according to the first embodiment transmits the generated volume data to the image storage device 120. When the medical image diagnostic device 110 transmits the volume data to the image storage device 120, the medical image diagnostic device 110 transmits supplementary information such as a patient ID identifying a patient, an inspection ID identifying an inspection, a device ID identifying the medical image diagnostic device 110, and a series ID identifying single shooting by the medical image diagnostic device 110, for example.

The image storage device 120 is a database that stores a medical image. Specifically, the image storage device 120 according to the first embodiment receives the volume data from the medical image diagnostic device 110, and stores the received volume data in a predetermined storage unit. Further, in the first embodiment, the workstation 130 generates a parallax image group based on the volume data, and transmits the generated parallax image group to the image storage device 120. Thus, the image storage device 120 stores the parallax image group transmitted from the workstation 130 in a predetermined storage unit. Further, in the present embodiment, the workstation 130 capable of storing a large amount of images may be used, and in this case, the image storage device 120 illustrated in FIG. 1 may be incorporated with the workstation 130 illustrated in FIG. 1. In other words, in the present embodiment, the volume data or the parallax image group may be stored in the workstation 130.

Further, in the first embodiment, the volume data or the parallax image group stored in the image storage device 120 is stored in association with the patient ID, the inspection ID, the device ID, the series ID, and the like. Thus, the workstation 130 or the terminal device 140 performs a search using the patient ID, the inspection ID, the device ID, the series ID, or the like, and acquires necessary volume data or a necessary parallax image group from the image storage device 120.

The workstation 130 is an image processing apparatus that performs image processing on a medical image. Specifically, the workstation 130 according to the first embodiment performs various rendering processes on the volume data acquired from the image storage device 120, and generates a parallax image group.

Further, the workstation 130 according to the first embodiment includes a monitor (which is referred to as a "stereoscopic display monitor" or "stereoscopic image display device") capable of displaying a stereoscopic image as a display unit. The workstation 130 generates a parallax image group and causes the generated parallax image group to be displayed on the stereoscopic display monitor. Thus, an operator of the workstation 130 can perform an operation of generating a parallax image group while checking a stereoscopically viewable stereoscopic image displayed on the stereoscopic display monitor.

Further, the workstation 130 transmits the generated parallax image group to the image storage device 120 or the terminal device 140. The workstation 130 transmits the supplementary information such as the patient ID, the inspection ID, the device ID, and the series ID, for example, when transmitting the parallax image group to the image storage device 120 or the terminal device 140. As supplementary information transmitted when the parallax image group is transmitted to the image storage device 120, supplementary information related to the parallax image group is further included. Examples of the supplementary information related to the parallax image group include the number of parallax images (for example, "9") and the resolution of a parallax image (for example, "466×350 pixels."

The terminal device 140 is a device that allows a doctor or a laboratory technician who works in the hospital to view a medical image. Examples of the terminal device 140 include a Personal Computer (PC), a tablet-type PC, a Personal Digital Assistant (PDA), and a portable telephone, which are operated by a doctor or a laboratory technician who works in the hospital. Specifically, the terminal device 140 according to the first embodiment includes a stereoscopic display monitor as a display unit. Further, the terminal device 140 acquires a parallax image group from the image storage device 120, and causes the acquired parallax image group to be displayed on the stereoscopic display monitor. As a result, a doctor or a laboratory technician who is an observer can view a stereoscopically viewable medical image. Alternatively, the terminal device 140 may be an arbitrary information processing terminal connected with a stereoscopic display monitor as an external device.

Here, the stereoscopic display monitor included in the workstation 130 or the terminal device 140 will be described. A general-purpose monitor which is currently most widely used two dimensionally displays a two-dimensional (2D) image and hardly performs a 3D display on a 2D image. If an observer desires a stereoscopic view to be displayed on the general-purpose monitor, a device that outputs an image to the general-purpose monitor needs to parallel-display a two-parallax image stereoscopically viewable to an observer through a parallel method or an intersection method. Alternatively, a device that outputs an image to the general-purpose monitor needs to display an image stereoscopically viewable to an observer through a color-complementation method using glasses in which a red cellophane is attached to a left-eye portion and a blue cellophane is attached to a right-eye portion.

Meanwhile, there are stereoscopic display monitors that allow a two-parallax image (which is also referred to as a "binocular parallax image") to be stereoscopically viewed using a dedicated device such as stereoscopic glasses.

Figure 2A:
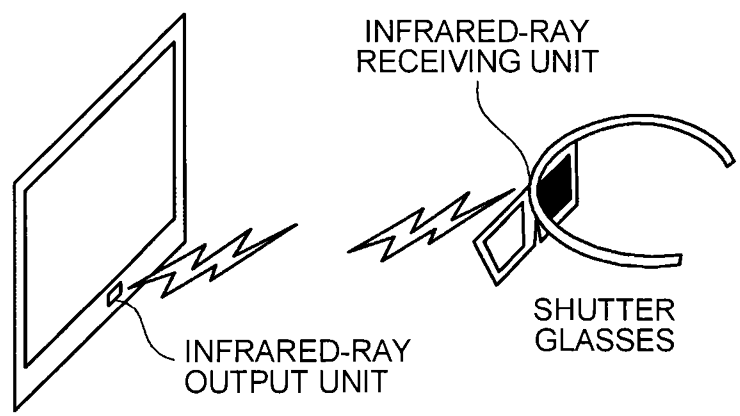
FIGS. 2A and 2B are diagrams for describing an example of a stereoscopic display monitor that performs a stereoscopic display based on a two-parallax image.
Figure 2B:
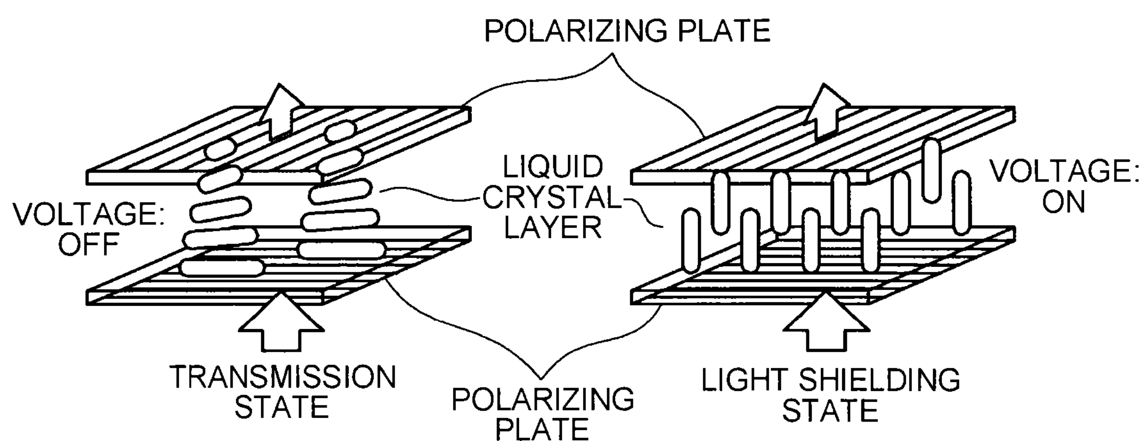

FIGS. 2A and 2B are diagrams for describing an example of a stereoscopic display monitor that performs a stereoscopic display based on a two-parallax image. In the example illustrated in FIGS. 2A and 2B, the stereoscopic display monitor performs a stereoscopic display by a shutter method, and shutter glasses are used as stereoscopic glasses worn by an observer who observes the monitor. The stereoscopic display monitor alternately outputs a two-parallax image in the monitor. For example, the monitor illustrated in FIG. 2A alternately outputs a left-eye image and a right-eye image with 120 Hz. As illustrated in FIG. 2A, the monitor includes an infrared-ray output unit, and controls an output of an infrared ray according to a timing at which images are switched.

The infrared ray output from the infrared-ray output unit is received by an infrared-ray receiving unit of the shutter glasses illustrated in FIG. 2A. A shutter is mounted to each of right and left frames of the shutter glasses, and the shutter glasses alternately switch a transmission state and a light shielding state of the right and left shutters according to a timing at which the infrared-ray receiving unit receives the infrared ray. A switching process of a transmission state and a light shielding state of the shutter will be described below.

As illustrated in FIG. 2B, each shutter includes an incident side polarizing plate and an output side polarizing plate, and further includes a liquid crystal layer disposed between the incident side polarizing plate and the output side polarizing plate. The incident side polarizing plate and the output side polarizing plate are orthogonal to each other as illustrated in FIG. 2B. Here, as illustrated in FIG. 2B, in an OFF state in which a voltage is not applied, light has passed through the incident side polarizing plate rotates at 90° due to an operation of the liquid crystal layer, and passes through the output side polarizing plate. In other words, the shutter to which a voltage is not applied becomes a transmission state.

Meanwhile, as illustrated in FIG. 2B, in an ON state in which a voltage is applied, a polarization rotation operation caused by liquid crystal molecules of the liquid crystal layer does not work, and thus light having passed through the incident side polarizing plate is shielded by the output side polarizing plate. In other words, the shutter to which a voltage is applied becomes a light shielding state.

In this regard, for example, the infrared-ray output unit outputs the infrared ray during a time period in which the left-eye image is being displayed on the monitor. Then, during a time period in which the infrared ray is being received, the infrared-ray receiving unit applies a voltage to the right-eye shutter without applying a voltage to the left-eye shutter. Through this operation, as illustrated in FIG. 2A, the right-eye shutter becomes the light shielding state, and the left-eye shutter becomes the transmission state, so that the left-eye image is incident to the left eye of the observer. Meanwhile, during a time period in which the right-eye image is being displayed on the monitor, the infrared-ray output unit stops an output of the infrared ray. Then, during a time period in which the infrared ray is not being received, the infrared-ray receiving unit applies a voltage to the left-eye shutter without applying a voltage to the right-eye shutter. Through this operation, the left-eye shutter becomes the light shielding state, and the right-eye shutter becomes the transmission state, so that the right-eye image is incident to the right eye of the observer. As described above, the stereoscopic display monitor illustrated in FIGS. 2A and 2B causes an image stereoscopically viewable to the observer to be displayed by switching an image to be displayed on the monitor in conjunction with the state of the shutter. A monitor employing a polarizing glasses method other than the shutter method is also known as the stereoscopic display monitor that allows a two-parallax image to be stereoscopically viewed.

Further, a stereoscopic display monitor that allows an observer to stereoscopically view a multi-parallax image with the naked eyes such as a nine-parallax image using a light beam controller such as a lenticular lens has been recently put to practical. This kind of stereoscopic display monitor makes a stereoscopic view possible by binocular parallax, and further makes a stereoscopic view possible by kinematic parallax in which an observed video changes with the movement of a point of view of an observer.

Figure 3:
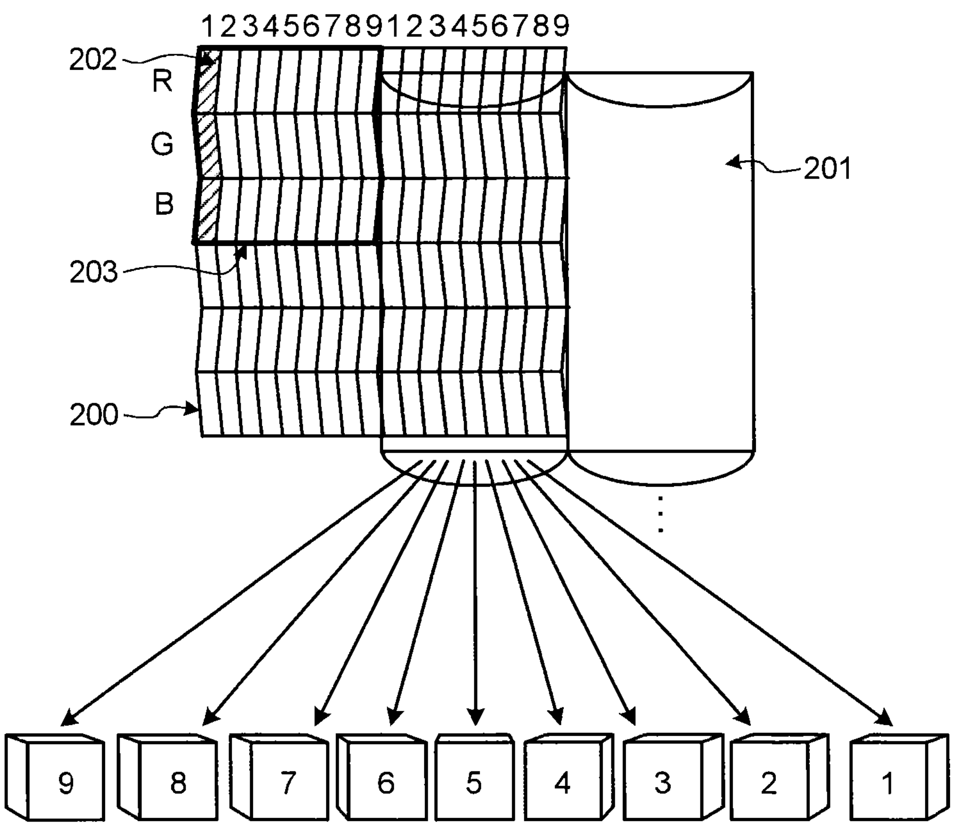
FIG. 3 is a diagram for describing an example of a stereoscopic display monitor that performs a stereoscopic display based on a nine-parallax image.

FIG. 3 is a diagram for describing an example of a stereoscopic display monitor that performs a stereoscopic display based on a nine-parallax image. In the stereoscopic display monitor illustrated in FIG. 3, a light beam controller is arranged in front of a planar display surface 200 such as a liquid crystal panel. For example, in the stereoscopic display monitor illustrated in FIG. 3, a vertical lenticular sheet 201 including an optical opening that extends in a vertical direction is attached to the front surface of the display surface 200 as the light beam controller. In the example illustrated in FIG. 3, the vertical lenticular sheet 201 is attached such that a convex portion thereof serves as the front surface, but the vertical lenticular sheet 201 may be attached such that a convex portion thereof faces the display surface 200.

As illustrated in FIG. 3, in the display surface 200, an aspect ratio is 3:1, and pixels 202 each of which includes three sub-pixels of red (R), green (G), and blue (B) arranged in a longitudinal direction are arranged in the form of a matrix. The stereoscopic display monitor illustrated in FIG. 3 converts a nine-parallax image including nine images into an interim image arranged in a predetermined format (for example, in a lattice form), and outputs the interim image to the display surface 200. In other words, the stereoscopic display monitor illustrated in FIG. 3 allocates nine pixels at the same position in the nine-parallax image to the pixels 202 of nine columns, respectively, and then performs an output. The pixels 202 of nine columns become a unit pixel group 203 to simultaneously display nine images having different point-of-view positions.

The nine-parallax image simultaneously output as the unit pixel group 203 in the display surface 200 is radiated as parallel light through a Light Emitting Diode (LED) backlight, and further radiated in multiple directions through the vertical lenticular sheet 201. As light of each pixel of the nine-parallax image is radiated in multiple directions, lights incident to the left eye and the right eye of the observer change in conjunction with the position (the position of the point of view) of the observer. In other words, depending on an angle at which the observer views, a parallax image incident to the right eye differs in a parallactic angle from a parallax image incident to the left eye. Through this operation, the observer can stereoscopically view a shooting target, for example, at each of nine positions illustrated in FIG. 3. For example, the observer can stereoscopically view, in a state in which the observer directly faces a shooting target, at the position of "5" illustrated in FIG. 3, and can stereoscopically view, in a state in which a direction of a shooting target is changed, at the positions other than "5" illustrated in FIG. 3. The stereoscopic display monitor illustrated in FIG. 3 is merely an example. The stereoscopic display monitor that displays the nine-parallax image may include a horizontal stripe liquid crystal of "RRR - - - , GGG - - - , and BBB - - - " as illustrated in FIG. 3 or may include a vertical stripe liquid crystal of "RGBRGB - - - ." Further, the stereoscopic display monitor illustrated in FIG. 3 may be of a vertical lens type in which a lenticular sheet is vertical as illustrated in FIG. 3 or may be of an oblique lens type in which a lenticular sheet is oblique.

The configuration example of the image processing system 1 according to the first embodiment has been briefly described so far. An application of the image processing system 1 described above is not limited to a case in which the PACS is introduced. For example, the image processing system 1 is similarly applied even to a case in which an electronic chart system for managing an electronic chart with a medical image attached thereto is introduced. In this case, the image storage device 120 serves as a database for managing an electronic chart. Further, for example, the image processing system 1 is similarly applied even to a case in which a Hospital Information System (HIS) or Radiology Information System (RIS) is introduced. Further, the image processing system 1 is not limited to the above-described configuration example. A function or an assignment of each device may be appropriately changed according to an operation form.

Figure 4:
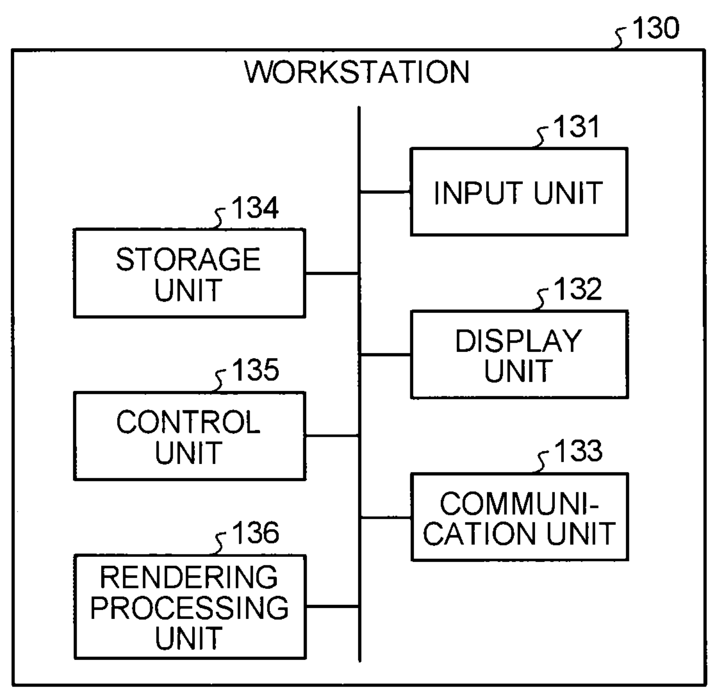
FIG. 4 is a diagram for describing a configuration example of a workstation according to the first embodiment.

Next, a configuration example of a workstation according to the first embodiment will be described with reference to FIG. 4. FIG. 4 is a diagram for describing a configuration example of a workstation according to the first embodiment. In the following, a "parallax image group" refers to an image group for a stereoscopic view generated by performing a volume rendering process on volume data. Further, a "parallax image" refers to each of images that configure the "parallax image group." In other words, the "parallax image group" is configured with a plurality of "parallax images" having different point-of-view positions.

The workstation 130 according to the first embodiment is a high-performance computer appropriate to image processing or the like, and includes an input unit 131, a display unit 132, a communication unit 133, a storage unit 134, a control unit 135, and a rendering processing unit 136 as illustrated in FIG. 4. In the following, a description will be made in connection with an example in which the workstation 130 is a high-performance computer appropriate to image processing or the like. However, the workstation 130 is not limited to this example, and may be an arbitrary information processing device. For example, the workstation 130 may be an arbitrary personal computer.

The input unit 131 includes a mouse, a keyboard, a trackball, or the like, and receives various operations which an operator has input on the workstation 130. Specifically, the input unit 131 according to the first embodiment receives an input of information used to acquire volume data which is a target of the rendering process from the image storage device 120. For example, the input unit 131 receives an input of the patient ID, the inspection ID, the device ID, the series ID, or the like. Further, the input unit 131 according to the first embodiment receives an input of a condition (hereinafter, referred to as a "rendering condition") related to the rendering process.

The display unit 132 includes a liquid crystal panel serving as a stereoscopic display monitor, and displays a variety of information. Specifically, the display unit 132 according to the first embodiment displays a Graphical User Interface (GUI), which is used to receive various operations from the operator, a parallax image group, or the like. The communication unit 133 includes a Network Interface Card (NIC) or the like and performs communication with other devices.

The storage unit 134 includes a hard disk, a semiconductor memory device, or the like, and stores a variety of information. Specifically, the storage unit 134 according to the first embodiment stores the volume data acquired from the image storage device 120 through the communication unit 133. Further, the storage unit 134 according to the first embodiment stores volume data which is under the rendering process, a parallax image group generated by the rendering process, or the like.

The control unit 135 includes an electronic circuit such as a Central Processing Unit (CPU), a Micro Processing Unit (MPU), or a Graphics Processing Unit (GPU) or an integrated circuit such as an Application Specific Integrated Circuit (ASIC) or a Field Programmable Gate Array (FPGA). The control unit 135 controls the workstation 130 in general.

For example, the control unit 135 according to the first embodiment controls a display of the GUI on the display unit 132 or a display of a parallax image group. Further, for example, the control unit 135 controls transmission/reception of the volume data or the parallax image group to/from the image storage device 120, which is performed through the communication unit 133. Further, for example, the control unit 135 controls the rendering process performed by the rendering processing unit 136. Further, for example, the control unit 135 controls an operation of reading volume data from the storage unit 134 or an operation of storing a parallax image group in the storage unit 134.

The rendering processing unit 136 performs various rendering processes on volume data acquired from the image storage device 120 under control of the control unit 135, and thus generates a parallax image group. Specifically, the rendering processing unit 136 according to the first embodiment reads volume data from the storage unit 134, and first performs pre-processing on the volume data. Next, the rendering processing unit 136 performs a volume rendering process on the pre-processed volume data, and generates a parallax image group. Subsequently, the rendering processing unit 136 generates a 2D image in which a variety of information (a scale, a patient name, an inspection item, and the like) is represented, and generates a 2D output image by superimposing the 2D image on each parallax image group. Then, the rendering processing unit 136 stores the generated parallax image group or the 2D output image in the storage unit 134. Further, in the first embodiment, the rendering process refers to the entire image processing performed on the volume data, and the volume rendering process a process of generating a 2D image in which 3D information is reflected during the rendering process. For example, the medical image generated by the rendering process corresponds to a parallax image.

Figure 5:
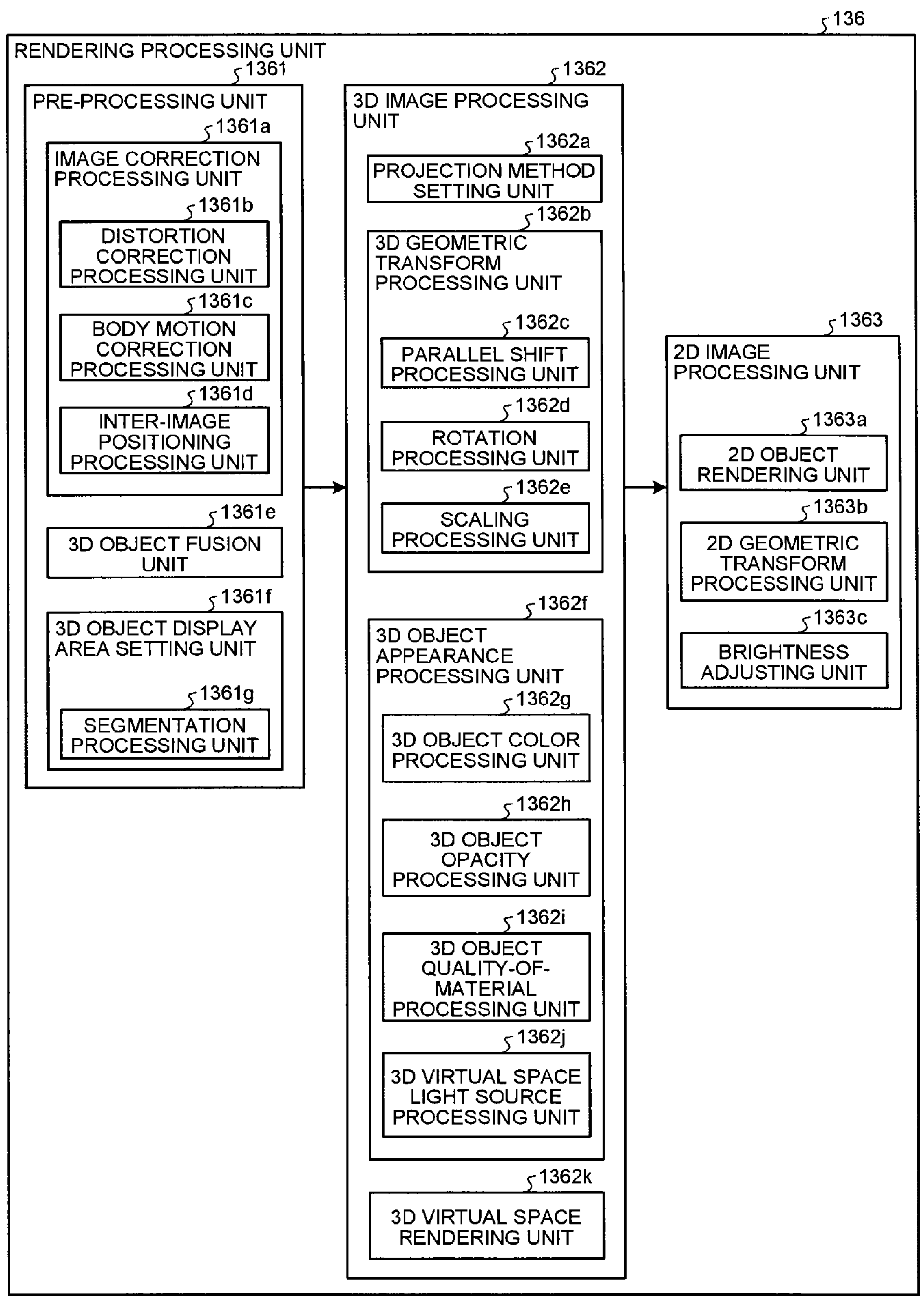
FIG. 5 is a diagram for describing a configuration example of a rendering processing unit illustrated in FIG. 4.

FIG. 5 is a diagram for describing a configuration example of the rendering processing unit illustrated in FIG. 4. As illustrated in FIG. 5, the rendering processing unit 136 includes a pre-processing unit 1361, a 3D image processing unit 1362, and a 2D image processing unit 1363. The pre-processing unit 1361 performs pre-processing on volume data. The 3D image processing unit 1362 generates a parallax image group from pre-processed volume data. The 2D image processing unit 1363 generates a 2D output image in which a variety of information is superimposed on a parallax image group. The respective units will be described below in order.

The pre-processing unit 1361 is a processing unit that performs a variety of pre-processing when performing the rendering process on volume data, and includes an image correction processing unit 1361*a*, a 3D object fusion unit 1361*e*, and a 3D object display area setting unit 1361*f*.

The image correction processing unit 1361*a* is a processing unit that performs an image correction process when processing two types of volume data as one volume data, and includes a distortion correction processing unit 1361*b*, a body motion correction processing unit 1361*c*, and an inter-image positioning processing unit 1361*d* as illustrated in FIG. 5. For example, the image correction processing unit 1361*a* performs an image correction process when processing volume data of a PET image generated by a PET-CT device and volume data of an X-ray CT image as one volume data. Alternatively, the image correction processing unit 1361*a* performs an image correction process when processing volume data of a T1-weighted image and volume data of a T2-weighted image which are generated by an MRI device as one volume data.

Further, the distortion correction processing unit 1361*b* corrects distortion of individual volume data caused by a collection condition at the time of data collection by the medical image diagnostic device 110. Further, the body motion correction processing unit 1361*c* corrects movement caused by body motion of a subject during a data collection time period used to generate individual volume data. Further, the inter-image positioning processing unit 1361*d* performs positioning (registration), for example, using a cross correlation method between two pieces of volume data which have been subjected to the correction processes by the distortion correction processing unit 1361*b* and the body motion correction processing unit 1361*c*.

The 3D object fusion unit 1361*e* performs the fusion of a plurality of volume data which have been subjected to the positioning by the inter-image positioning processing unit 1361*d*. Further, the processes performed by the image correction processing unit 1361*a* and the 3D object fusion unit 1361*e* may not be performed when the rendering process is performed on single volume data.

The 3D object display area setting unit 1361*f* is a processing unit that sets a display area corresponding to a display target organ designated by an operator, and includes a segmentation processing unit 1361*g*. The segmentation processing unit 1361*g* is a processing unit that extracts an organ, such as a heart, a lung, or a blood vessel, which is designated by the operator, for example, by an area extension technique based on a pixel value (voxel value) of volume data.

Further, the segmentation processing unit 1361*g* does not perform the segmentation process when a display target organ has not been designated by the operator. Further, the segmentation processing unit 1361*g* extracts a plurality of corresponding organs when a plurality of display target organs are designated by the operator. Further, the process performed by the segmentation processing unit 1361*g* may be re-executed at a fine adjustment request of the operator who has referred to a rendering image.

The 3D image processing unit 1362 performs the volume rendering process on the pre-processed volume data which has been subjected to the process performed by the pre-processing unit 1361. As processing units for performing the volume rendering process, the 3D image processing unit 1362 includes a projection method setting unit 1362*a*, a 3D geometric transform processing unit 1362*b*, a 3D object appearance processing unit 1362*f*, and a 3D virtual space rendering unit 1362*k*.

The projection method setting unit 1362*a* determines a projection method for generating a parallax image group. For example, the projection method setting unit 1362*a* determines whether the volume rendering process is to be executed using a parallel projection method or a perspective projection method.

The 3D geometric transform processing unit 1362*b* is a processing unit that determines information necessary to perform 3D geometric transform on volume data which is to be subjected to the volume rendering process, and includes a parallel shift processing unit 1362*c*, a rotation processing unit 1362*d*, and a scaling processing unit 1362*e*. The parallel shift processing unit 1362*c* is a processing unit that determines a shift amount to shift volume data in parallel when a point-of-view position is shifted in parallel at the time of the volume rendering process. The rotation processing unit

1362*d* is a processing unit that determines a movement amount for rotationally moving volume data when a point-of-view position is rotationally moved at the time of the volume rendering process. Further, the scaling processing unit 1362*e* is a processing unit that determines an enlargement ratio or a reduction ratio of volume data when it is requested to enlarge or reduce a parallax image group.

The 3D object appearance processing unit 1362*f* includes a 3D object color processing unit 1362*g*, a 3D object opacity processing unit 1362*h*, a 3D object quality-of-material processing unit 1362*i*, and a 3D virtual space light source processing unit 1362*j*. The 3D object appearance processing unit 1362*f* performs a process of determining a display form of a parallax image group to be displayed through the above processing units, for example, according to the operator's request.

The 3D object color processing unit 1362*g* is a processing unit that determines a color colored to each area segmented from volume data. The 3D object opacity processing unit 1362*h* is a processing unit that determines opacity of each voxel configuring each area segmented from volume data. In volume data, an area behind an area having opacity of "100%" is not represented in a parallax image group. Further, in volume data, an area having opacity of "0%" is not represented in a parallax image group.

The 3D object quality-of-material processing unit 1362*i* is a processing unit that determines the quality of a material of each area segmented from volume data and adjusts the texture when the area is represented. The 3D virtual space light source processing unit 1362*j* is a processing unit that determines the position or the type of a virtual light source installed in a 3D virtual space when the volume rendering process is performed on volume data. Examples of the type of a virtual light source include a light source that emits a parallel beam from infinity and a light source that emits a radial beam from a point of view.

The 3D virtual space rendering unit 1362*k* performs the volume rendering process on volume data, and generates a parallax image group. Further, the 3D virtual space rendering unit 1362*k* uses a variety of information, which is determined by the projection method setting unit 1362*a*, the 3D geometric transform processing unit 1362*b*, and the 3D object appearance processing unit 1362*f*, as necessary when the volume rendering process is performed.

Here, the volume rendering process performed by the 3D virtual space rendering unit 1362*k* is performed according to the rendering condition. For example, the parallel projection method or the perspective projection method may be used as the rendering condition. Further, for example, a reference point-of-view position, a parallactic angle, and a parallax number may be used as the rendering condition. Further, for example, a parallel shift of a point-of-view position, a rotational movement of a point-of-view position, an enlargement of a parallax image group, and a reduction of a parallax image group may be used as the rendering condition. Further, for example, a color colored, transparency, the texture, the position of a virtual light source, and the type of virtual light source may be used as the rendering condition. The rendering condition may be input by the operator through the input unit 131 or may be initially set. In either case, the 3D virtual space rendering unit 1362*k* receives the rendering condition from the control unit 135, and performs the volume rendering process on volume data according to the rendering condition. Further, at this time, the projection method setting unit 1362*a*, the 3D geometric transform processing unit 1362*b*, and the 3D object appearance processing unit 1362*f* determine a variety of necessary information according to the rendering condition, and thus the 3D virtual space rendering unit 1362*k* generates a parallax image group using a variety of information determined.

Figure 6:
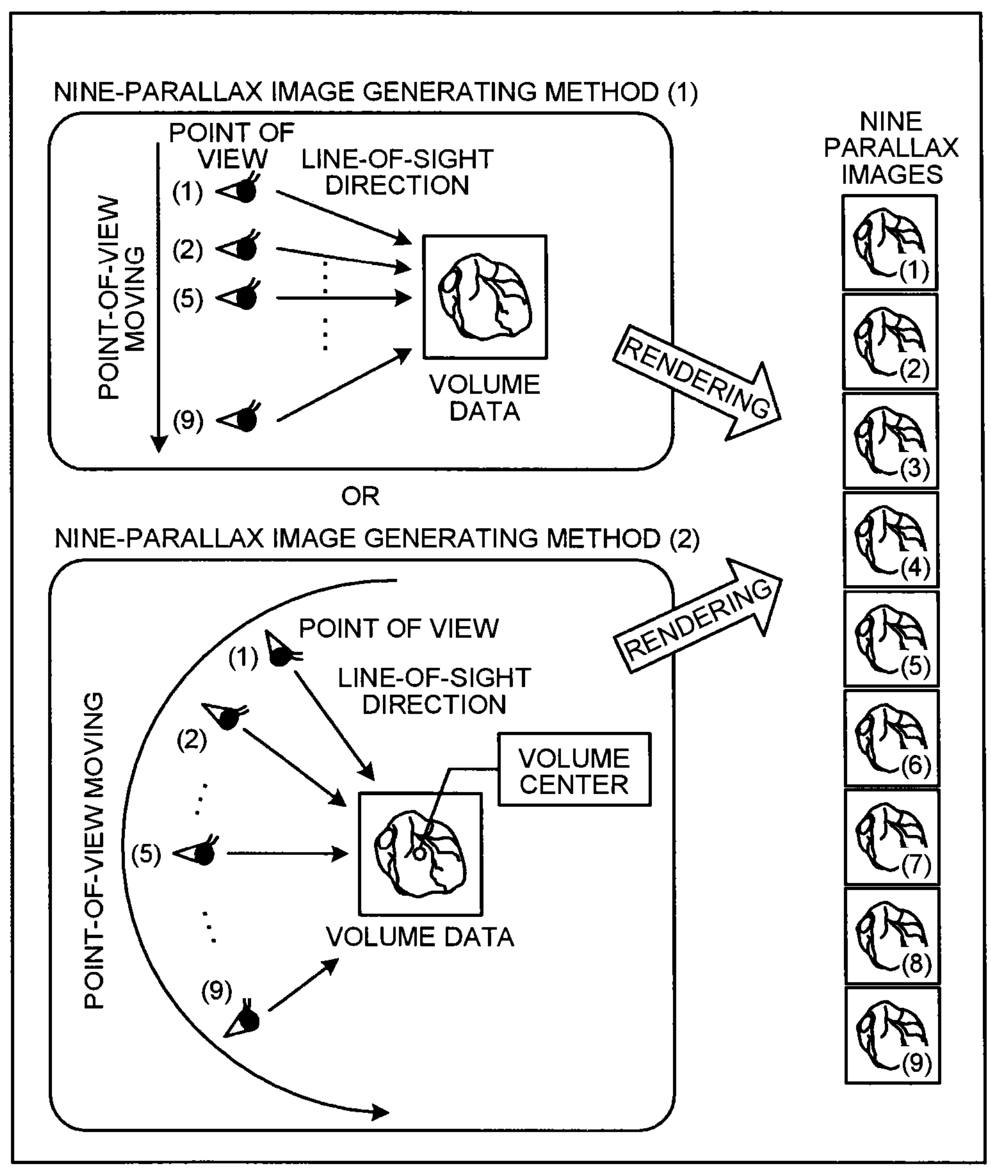
FIG. 6 is a diagram for describing an example of a volume rendering process according to the first embodiment.

FIG. 6 is a diagram for describing an example of the volume rendering process according to the first embodiment. For example, let us assume that the 3D virtual space rendering unit 1362*k* receives the parallel projection method as the rendering condition, and further receives a reference point-of-view position (5) and a parallactic angle "1°" as illustrated in a "nine-parallax image generating method (1)" of FIG. 6. In this case, the 3D virtual space rendering unit 1362*k* shifts the position of a point of view to (1) to (9) in parallel so that the parallactic angle can be changed by "1°", and generates nine parallax images between which the parallactic angle (an angle in a line-of-sight direction) differs from each other by 1° by the parallel projection method. Further, when the parallel projection method is performed, the 3D virtual space rendering unit 1362*k* sets a light source that emits a parallel beam in a line-of-sight direction from infinity.

Alternatively, the 3D virtual space rendering unit 1362*k* receives the perspective projection method as the rendering condition, and further receives a reference point-of-view position (5) and a parallactic angle "1°" as illustrated in a "nine-parallax image generating method (2)" of FIG. 6. In this case, the 3D virtual space rendering unit 1362*k* rotationally moves the position of a point of view to (1) to (9) so that the parallactic angle can be changed by "1°" centering on the center (gravity center) of volume data, and generates nine parallax images between which the parallactic angle differs from each other by 1° by the perspective projection method. Further, when the perspective projection method is performed, the 3D virtual space rendering unit 1362*k* sets a point light source or a surface light source, which three-dimensionally emits light in a radial manner centering on a line-of-sight direction, at each point of view. Further, when the perspective projection method is performed, the points of view (1) to (9) may be parallel-shifted according to the rendering condition.

Further, the 3D virtual space rendering unit 1362*k* may perform the volume rendering process using the parallel projection method and the perspective projection method together by setting a light source that two-dimensionally emits light in a radial manner centering on the line-of-sight direction on a longitudinal direction of a volume rendering image to display, and emits a parallel beam in the line-of-sight direction from infinity on a transverse direction of a volume rendering image to display.

The nine parallax images generated in the above-described way configure a parallax image group. In the first embodiment, for example, the nine parallax images are converted into interim images arranged in a predetermined format (for example, a lattice form) by the control unit 135, and then output to the display unit 132 serving as the stereoscopic display monitor. At this time, the operator of the workstation 130 can perform an operation of generating a parallax image group while checking a stereoscopically viewable medical image displayed on the stereoscopic display monitor.

The example of FIG. 6 has been described in connection with the case in which the projection method, the reference point-of-view position, and the parallactic angle are received as the rendering condition. However, similarly even when any other condition is received as the rendering condition, the 3D virtual space rendering unit 1362*k* generates the parallax image group while reflecting each rendering condition.

Further, the 3D virtual space rendering unit 1362*k* further has a function of performing a Multi Planer Reconstruction (MPR) technique as well as the volume rendering and reconstructing an MPR image from volume data. The 3D virtual space rendering unit 1362*k* further has a function of performing a "curved MPR" and a function of performing "intensity projection."

Subsequently, the parallax image group which the 3D image processing unit 1362 has generated based on the volume data is regarded as an underlay. Then, an overlay in which a variety of information (a scale, a patient name, an inspection item, and the like) is represented is superimposed on the underlay, so that a 2D output image is generated. The 2D image processing unit 1363 is a processing unit that performs image processing on the overlay and the underlay and generates a 2D output image, and includes a 2D object rendering unit 1363*a*, a 2D geometric transform processing unit 1363*b*, and a brightness adjusting unit 1363*c* as illustrated in FIG. 5. For example, in order to reduce a load required in a process of generating a 2D output image, the 2D image processing unit 1363 generates nine 2D output images by superimposing one overlay on each of nine parallax images (underlays). In the following, an underlay on which an overlay is superimposed may be referred to simply as a "parallax image."

The 2D object rendering unit 1363*a* is a processing unit that renders a variety of information represented on the overlay. The 2D geometric transform processing unit 1363*b* is a processing unit that parallel-shifts or rotationally moves the position of a variety of information represented on the overlay, or enlarges or reduces a variety of information represented on the overlay.

The brightness adjusting unit 1363*c* is a processing unit that performs a brightness converting process. For example, the brightness adjusting unit 1363*c* adjusts brightness of the overlay and the underlay according to an image processing parameter such as gradation of a stereoscopic display monitor of an output destination, a window width (WW), or a window level (WL).

For example, the control unit 135 stores the 2D output image generated as described above in the storage unit 134, and then transmits the 2D output image to the image storage device 120 through the communication unit 133. Then, for example, the terminal device 140 acquires the 2D output image from the image storage device 120, converts the 2D output image into an interim image arranged in a predetermined format (for example, a lattice form), and displays the interim image on the stereoscopic display monitor. Further, for example, the control unit 135 stores the 2D output image in the storage unit 134, then transmits the 2D output image to the image storage device 120 through the communication unit 133, and transmits the 2D output image to the terminal device 140. Then, the terminal device 140 converts the 2D output image transmitted from the workstation 130 into the interim image arranged in a predetermined format (for example, a lattice form), and causes the interim image to be displayed on the stereoscopic display monitor. Through this operation, a doctor or a laboratory technician who uses the terminal device 140 can view a stereoscopically viewable medical image in a state in which a variety of information (a scale, a patient name, an inspection item, and the like) is represented.

Figure 7:
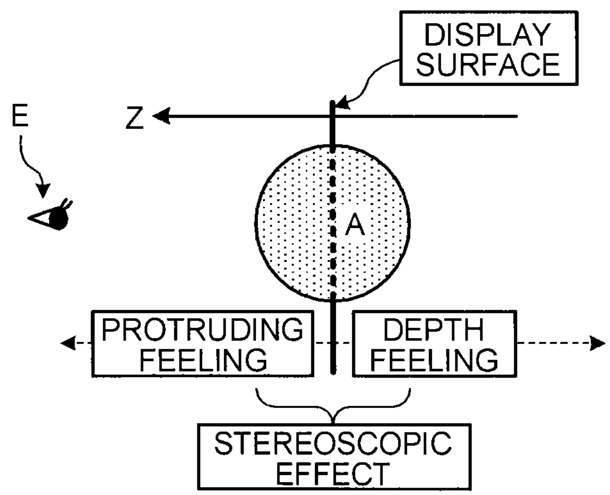
FIG. 7 is a diagram for describing a stereoscopic image space.

Further, as described above, the stereoscopic display monitor according to the first embodiment displays a stereoscopic image stereoscopically viewable to the observer by displaying a plurality of parallax images. For example, the stereoscopic display monitor displays an organ of a subject or the like through a stereoscopic image. Through this operation, the observer who observes the stereoscopic display monitor can stereoscopically view an organ of a subject or the like. The stereoscopic image is displayed in a "stereoscopic image space" which is formed to represent a space before and after the display surface of the stereoscopic display monitor. The stereoscopic image space will be described with reference to FIG. 7. FIG. 7 is a diagram for describing a stereoscopic image space.

The observer who views the parallax image group displayed on the stereoscopic display monitor stereoscopically views a stereoscopic image A in a stereoscopic image space as illustrated in FIG. 7. A stereoscopic effect which the observer feels is broadly classified into a protruding feeling and a depth feeling as illustrated in FIG. 7. The protruding feeling is a feeling which the observer feels as if a stereoscopic image protrudes from the display surface of the stereoscopic display monitor in a direction closer to the observer's point of view (the observer's point of view E). Further, the depth feeling is a feeling which the observer feels as if a stereoscopic image is recessed from the display surface of the stereoscopic display monitor in a direction away from the observer's point of view (the observer's point of view E).

Figure 8:
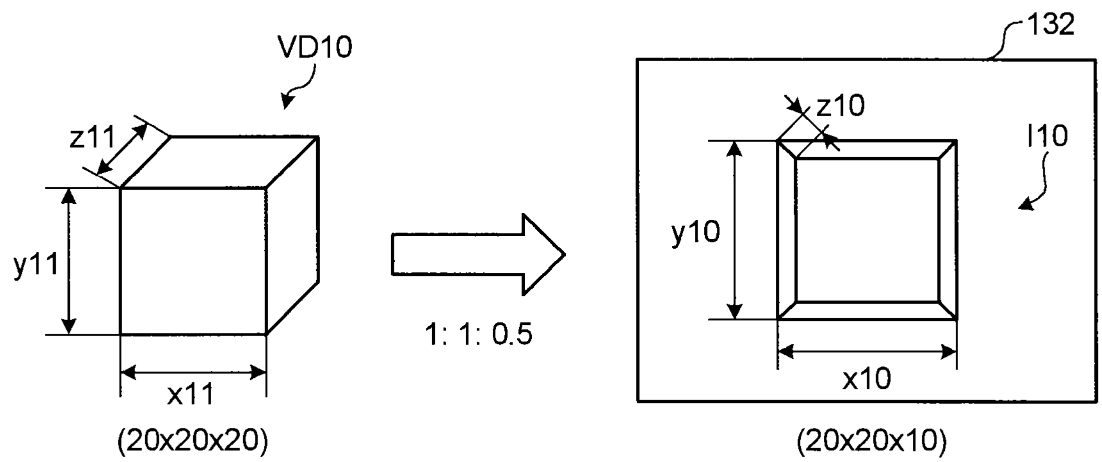
FIG. 8 is a diagram illustrating an example of a stereoscopic image displayed by a stereoscopic display monitor.
Figure 8:
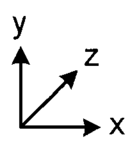

Here, generally, when a blurred image in which an image is seen double is not generated, the ratio of the size of the stereoscopic image displayed by the stereoscopic display monitor in a longitudinal direction, a traverse direction, and a depth direction is different from the ratio of the size of an actual subject in a longitudinal direction, a traverse direction, and a depth direction in many cases. Specifically, the size of a stereoscopic image, displayed by the stereoscopic display monitor, in the depth direction can be extended by increasing the parallactic angle. However, when the parallactic angle is too increased, a pseudo image (a so-called "blurred image") is generated. For this reason, when the parallactic angle is realistically determined in a range in which an image having no blur is displayed, and the parallax image group is generated based on the parallactic angle determined in this way, a component in the depth direction in the stereoscopic image displayed by the stereoscopic display monitor is often more compressed than in an actual subject. In other words, the observer sees the stereoscopic image, displayed by the stereoscopic display monitor, which is crushed in the depth direction. This point will be concretely described with reference to FIG. 8. FIG. 8 is a diagram illustrating an example of a stereoscopic image displayed by a stereoscopic display monitor. In the following, the ratio of the size in the longitudinal direction, the traverse direction, and the depth direction is sometimes referred to as a "three-direction ratio."

In the example illustrated in FIG. 8, it is assumed that the rendering processing unit 136 performs the rendering process on volume data VD10 based on nine different point-of-view positions, and the display unit 132 which is the stereoscopic display monitor displays nine parallax images generated by the rendering processing unit 136.

The volume data VD10 is a set of voxels, and each voxel is assigned with a predetermined pixel value, coordinates on a 3D virtual space, a voxel size (for example, 1 voxel=1 mm angle) corresponding to an actual size of a subject, and the like. In other words, by mapping each voxel included in the volume data in the 3D virtual space, a subject image of an actual size can be three-dimensionally reconstructed. It is assumed that the volume data VD10 illustrated in FIG. 8 is in a state in which mapping has been performed in the 3D virtual space and has the actual size of a subject. In the following, a subject image with an actual size three-dimensionally represented by volume data is sometimes referred to as a "3D subject image."

In the example illustrated in FIG. 8, it is assumed that in the 3D subject image represented by the volume data VD10, "x11×y11×z11" which is the size of "traverse direction (x direction)×longitudinal direction (y direction)×depth direction (z direction)" is "20 cm×20 cm×20 cm." In other words, the three-direction ratio of the volume data VD10 is "1:1:1."

However, when the parallax image group is generated from the volume data VD10 based on the parallactic angle determined in a range in which an image having no blur is displayed, and the generated parallax image group is displayed by the display unit 132, the three-direction ratio of the stereoscopic image viewed by the observer is different from the three-direction ratio "1:1:1" of the volume data VD10 in many cases. For example, in the example illustrated in FIG. 8, a stereoscopic image I10 is "20 cm" in the size (x10) in the traverse direction, "20 cm" in the size (y10) in the longitudinal direction, and "10 cm" in the size (z10) in the depth direction. In this example, since the parallactic angle is determined in a range in which an image having no blur is displayed, the stereoscopic image I10 is equal in the sizes in the traverse direction and the longitudinal direction to the volume data VD10, but is "0.5 times" the volume data VD10 in the size in the depth direction. In other words, the scale of the stereoscopic image I10 to the volume data VD10 is "once (unmagnified)" in the traverse direction and the longitudinal direction but is "0.5 times" in the depth direction.

Since the parallactic angle is determined in a range in which an image having no blur is displayed as described above, a scale of the stereoscopic image to the volume data is not equal in the traverse direction, the longitudinal direction, and the depth direction in many cases, and the stereoscopic image displayed by the display unit 132 is more compressed in the size in the depth direction rather than the traverse direction and the longitudinal direction compared with the 3D subject image in many cases. For this reason, it is difficult for the observer to understand the ratio of the size of the subject in each direction. For example, when a stereoscopic image in which an organ, a blood vessel, or the like is arranged at a different position in the depth direction is displayed on the stereoscopic display monitor, and the size of the stereoscopic image in the depth direction is compressed, it is difficult for the observer to understand a sense of distance between an organ and a blood vessel.

In the first embodiment, the workstation 130 can cause the stereoscopic image, which has substantially the same three-direction ratio as the three-direction ratio of the 3D subject image represented by the volume data, to be displayed on the display unit 132.

Specifically, the control unit 135 of the workstation 130 acquires the ratio of the scales of the stereoscopic image to the 3D subject image in the traverse direction, the longitudinal direction, and the depth direction. Then, the control unit 135 controls the rendering processing unit 136 based on the acquired ratio of the scales in the respective directions such that volume data is reduced or enlarged so that the ratio of the sizes of the 3D subject image in the traverse direction, the longitudinal direction, and the depth direction can be substantially the same as the ratio of the sizes of the stereoscopic image in the traverse direction, the longitudinal direction, and the depth direction. Then, the control unit 135 controls the rendering processing unit 136 such that the rendering process is performed on the reduced or enlarged volume data.

The control unit 135 according to the first embodiment will be described below in detail. The following will be described in connection with an example in which each time volume data is generated by the medical image diagnostic device 110, the workstation 130 performs the rendering process on the generated volume data to generate nine parallax images, and performs display control such that the generated nine parallax images are displayed on the display unit 132. Further, the following description will be described in connection with an example in which a parallax image group is generated by the perspective projection method as in the example illustrated in the "nine-parallax image generating method (2)" of FIG. 6.

Figure 9:
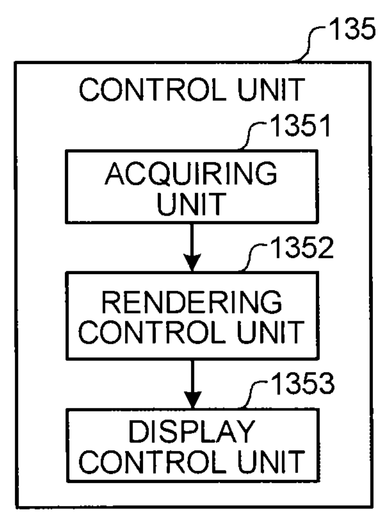
FIG. 9 is a diagram for describing a configuration example of a control unit according to the first embodiment.

FIG. 9 is a diagram for describing a configuration example of the control unit 135 according to the first embodiment. As illustrated in FIG. 9, the control unit 135 includes an acquiring unit 1351, a rendering control unit 1352, and a display control unit 1353.

The acquiring unit 1351 acquires a scale ratio which is a ratio of a scale in the depth direction (z direction) to the display surface of the display unit 132 and a scale in another direction which is a direction other than the depth direction among scales of a stereoscopic image assumed to be displayed on the display unit 132 using a parallax image group obtained from volume data. For example, in the example illustrated in FIG. 8, the acquiring unit 1351 acquires "1:1:0.5" as the scale ratio of the traverse direction (x direction), the longitudinal direction (y direction), and the depth direction (z direction). The scale ratio is determined based on the parallactic angle or the like, which will be described later.

The rendering control unit 1352 generates a parallax image group based on volume data in cooperation with the rendering processing unit 136. Specifically, the rendering control unit 1352 according to the first embodiment controls the rendering processing unit 136 based on the scale ratio acquired by the acquiring unit 1351 such that volume data is reduced or enlarged so that the scale of the stereoscopic image in the depth direction (z direction) can be substantially the same as the scale in another direction, and further controls the rendering processing unit 136 such that the rendering process is performed on the reduced or enlarged volume data.

For example, when the scale ratio "1:1:0.5" is acquired by the acquiring unit 1351 as in the above example, the rendering control unit 1352 causes the rendering processing unit 136 to generate volume data whose three-direction ratio is "0.5:0.5:1" based on the scale ratio "1:1:0.5" so that the scales of the stereoscopic image in the traverse direction (x direction), the longitudinal direction (y direction), and the depth direction (z direction) can be "1:1:1." Thus, the rendering processing unit 136 generates reduces or enlarges the volume data according to an instruction of the rendering control unit 1352, and generates volume data whose three-direction ratio is "0.5:0.5:1."

Further, the rendering processing unit 136 according to the first embodiment does not reduce or enlarge the volume data generated by the medical image diagnostic device 110, and newly generates reduced or enlarged virtual volume data while maintaining the volume data generated by the medical image diagnostic device 110. In the following, virtual volume data generated by the rendering processing unit 136 is sometimes referred to as "virtual volume data." As described above, the rendering processing unit 136 according to the first embodiment functions as a "transform unit" that generates virtual volume data in which the size of volume data is transformed.

The display control unit 1353 causes a plurality of parallax images, which are generated by the rendering processing unit 136 under control of the rendering control unit 1352, to be displayed on the display unit 132. Through this operation, the observer views a stereoscopic image displayed by the display unit 132 using the plurality of parallax images generated by the rendering processing unit 136.

An example of a process performed by the acquiring unit 1351, the rendering control unit 1352, and the display control unit 1353 will be described below with reference to FIGS. 8, 10, and 11.

First, the acquiring unit 1351 acquires a parallactic angle which is a rendering condition. At this time, when the parallactic angle which is the rendering condition has been determined on a system in advance, the acquiring unit 1351 acquires the parallactic angle from a predetermined storage unit in which system information is stored. Further, when the parallactic angle has been set by the observer (operator), the acquiring unit 1351 acquires the parallactic angle from a predetermined storage unit in which setting information is stored.

Then, the acquiring unit 1351 acquires the scale of a stereoscopic image, which is assumed to be displayed on the display unit 132 using a parallax image group obtained from volume data to be processed, using a predetermined parameter represented by the acquired parallactic angle. At this time, when a parallax image group is actually generated based on not volume data to be processed but the acquired parallactic angle, the acquiring unit 1351 acquires the scale of the stereoscopic image assumed to be viewed by the observer when the parallax image group is displayed on the display unit 132. The acquiring unit 1351 according to the first embodiment acquires the ratio of the scale of the stereoscopic image to the 3D subject image in the traverse direction, the scale in the longitudinal direction, and the scale in the depth direction using a parameter "a(θ)" represented by a parallactic angle (θ) as the "scale ratio."

For example, it is assumed that the size of "traverse direction×longitudinal direction×depth direction" of the 3D subject image is "X×Y×Z," and the display size (display magnification) of the display unit 132 is set to "once (unmagnified)" in which the 3D subject image is displayed with the actual size. In this case, for example, the display unit 132 displays a 3D subject image of "X×Y×a(θ)·Z" as a stereoscopic image. In this example, the scale ratio is "1:1:a(θ)." In other words, the parameter "a(θ)" represents the ratio of the scale in the traverse direction (x direction) and the scale in the depth direction (z direction), and represents the ratio of the scale in the longitudinal direction (y direction) and the scale in the depth direction (z direction). The acquiring unit 1351 can acquire the "scale ratio" using the parameter "a(θ)."

The description will proceed with reference to the example illustrated in FIG. 8. The acquiring unit 1351 acquires the parallactic angle θ used at the time of the rendering process, and acquires the parameter "a(θ)=0.5" based on the acquired parallactic angle θ. Through this operation, when the parallax image group is generated from the volume data VD10 based on the parallactic angle θ, the acquiring unit 1351 acquires "1:1:0.5" as the scale ratio of the stereoscopic image I10 assumed to be displayed on the display unit 132 using the parallax image group.

Further, the workstation 130 may store the scale ratio corresponding to the parallactic angle in a predetermined storage unit. In this case, the acquiring unit 1351 can acquire the scale ratio corresponding to the parallactic angle from the predetermined storage unit.

Subsequently, since the scale ratio "1:1:0.5" is acquired by the acquiring unit 1351, the rendering control unit 1352 controls the rendering processing unit 136 such that virtual volume data whose three-direction ratio is "0.5:0.5:1" is generated so that the scale ratio of the stereoscopic image displayed on the display unit 132 can be substantially the same. In other words, the rendering control unit 1352 controls the rendering processing unit 136 such that virtual volume data whose three-direction ratio is "0.5:0.5:1" is generated so that the three-direction ratio of the 3D subject image can be substantially the same as the three-direction ratio of the stereoscopic image. Through this operation, the scaling processing unit **1362*e* of the rendering processing unit 136** determines to set the reduction ratio of the volume data in the traverse direction (x direction) to "0.5", determines to set the reduction ratio of the volume data in the longitudinal direction (y direction) to "0.5", and determines to set the reduction ratio of the volume data in the depth direction (z direction) to "1."

At this time, the rendering processing unit 136 sets a direction toward volume data from the point-of-view position at the time of the rendering process as the depth direction, and reduces or enlarges the volume data. For example, when the rendering condition is the perspective projection method, the 3D virtual space rendering unit **1362*k* of the rendering processing unit 136 generates virtual volume data by rotationally moving the volume data based on the movement amount determined by the rotation processing unit 1362*d* and then reducing or enlarging volume data based on the enlargement ratio or the reduction ratio determined by the scaling processing unit 1362*e*, and then performs the volume rendering process on the generated virtual volume data. Further, when the rendering condition is the parallel projection method, the 3D virtual space rendering unit 1362*k* does not necessarily rotationally move volume data even if the point-of-view position is changed. Thus, the 3D virtual space rendering unit 1362*k*** sets a direction toward the volume data from the point-of-view position at the time of the rendering process as the depth direction (z direction), and reduces or enlarges the volume data.

Here, an example of a process performed by the rendering processing unit 136 will be described with reference to FIG. 10. FIG. 10 is a diagram for describing an example of a process performed by the rendering processing unit 136 according to the first embodiment. Actually, the rendering process is performed on the volume data VD10 at nine point-of-view positions, but FIG. 10 illustrates the rendering process performed at two point-of-view positions as an example. In the following, it is assumed that the rendering control unit 1352 controls the rendering processing unit 136 such that virtual volume data whose three-direction ratio is "0.5:0.5:1" is generated. In other words, the scaling processing unit **1362*e*** determines to set the enlargement ratio or the reduction ratio of the volume data in the respective directions to "0.5:0.5:1."

Figure 10:
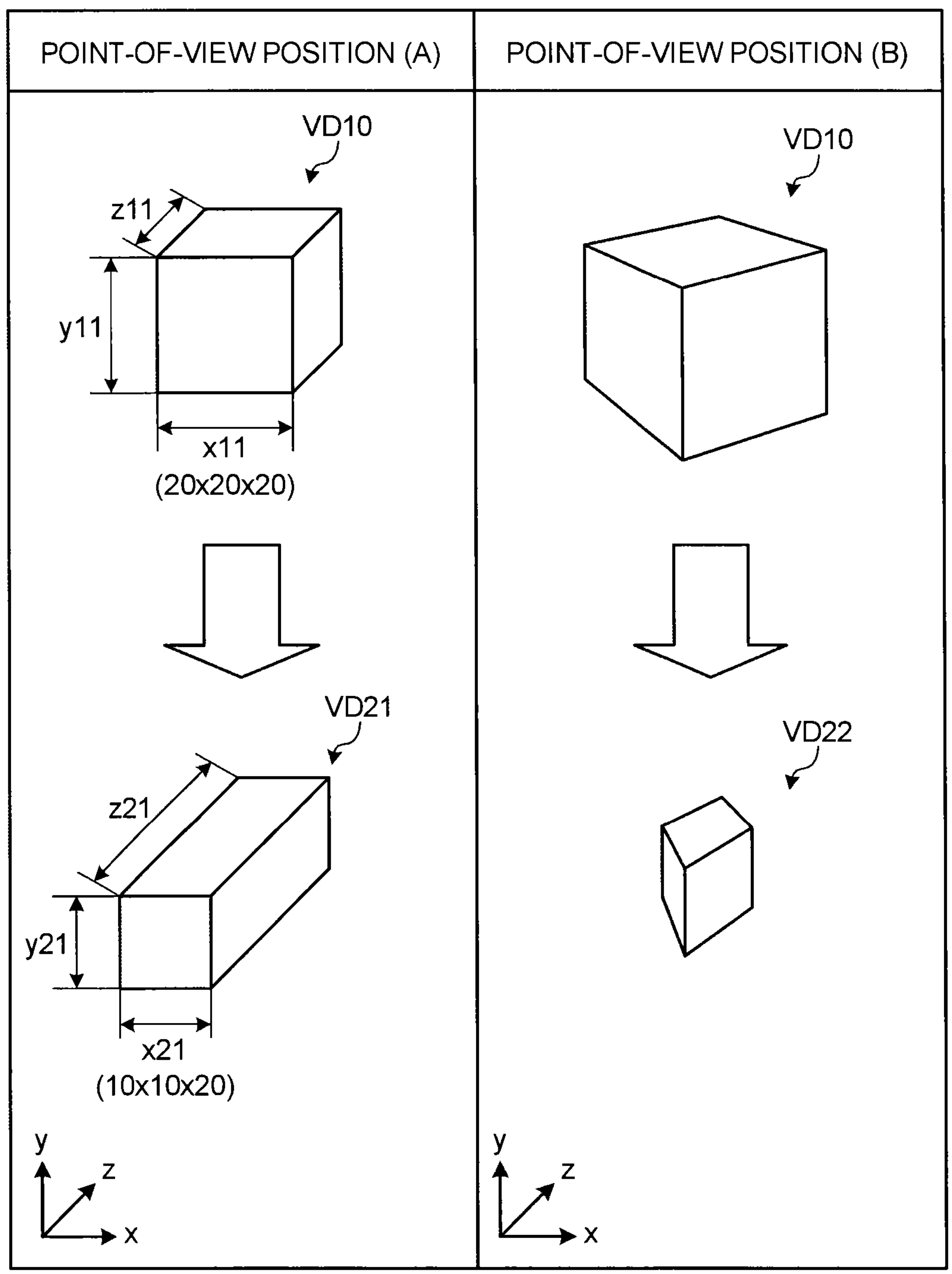
FIG. 10 is a diagram for describing an example of a process performed by a rendering processing unit 136 according to the first embodiment.

In an example illustrated in a point-of-view position (A) of FIG. 10, the volume data VD10 is assumed to be in a state in which rotational movement is performed by the 3D virtual space rendering unit **1362*k* so that a direction toward the volume data VD10 from the point-of-view position (A) can become the depth direction (z direction). Further, the volume data VD10 illustrated in the point-of-view position (A) of FIG. 10 is assumed that the size of "traverse direction×longitudinal direction×depth direction" is "20 cm×20 cm×20 cm." In other words, the three-direction ratio of the volume data VD10 is "1:1:1." In this case, the 3D virtual space rendering unit 1362***k* generates virtual volume data VD21 whose three-direction ratio is "0.5:0.5:1" based on the enlargement ratio or the reduction ratio determined by the scaling processing unit 1362*e*.

In the example illustrated in FIG. 10, the 3D virtual space rendering unit 1362*k* generates the virtual volume data VD21 by reducing the size of the volume data VD10 in the traverse direction to "0.5 times" and reducing the size in the longitudinal direction to "0.5 times." In other words, the 3D virtual space rendering unit 1362*k* generates the virtual volume data VD21 whose size in the xyz directions is "10 cm×10 cm×20 cm" from the virtual volume data VD10 whose size in the xyz directions is "20 cm×20 cm×20 cm." The rendering processing unit 136 performs the volume rendering process on the generated the virtual volume data VD22 as described above.

Similarly, in an example illustrated in a point-of-view position (B) of FIG. 10, the volume data VD10 is assumed to be in a state in which rotational movement is performed by the 3D virtual space rendering unit 1362*k* so that a direction toward the volume data VD10 from the point-of-view position (B) can become the depth direction (z direction). In this case, the 3D virtual space rendering unit 1362*k* generates virtual volume data VD22 by reducing the size of the volume data VD10 in the traverse direction in the state illustrated in the point-of-view position (B) of FIG. 10 to "0.5 times" and reducing the size in the longitudinal direction to "0.5 times."

In this way, the rendering control unit 1352 generates virtual volume data at nine point-of-view positions and then controls the rendering processing unit 136 such that the volume rendering process is performed on virtual volume data. The nine parallax images generated by the rendering processing unit 136 are ones in which a 3D subject image, in which the size in the depth direction is twice extended compared to a 3D subject image represented by volume data, is reflected. However, since the scale ratio is "1:1:0.5," the stereoscopic image displayed on the display unit 132 using the nine parallax images is compressed to "0.5 times" in the size in the depth direction. In other words, a stereoscopic image stereoscopically viewed to the observer has the three-direction ratio of "1:1:1" similarly to the 3D subject image represented by the volume data.

Subsequently, the display control unit 1353 causes a plurality of parallax images generated by the rendering processing unit 136 as described above to be displayed on the display unit 132. FIG. 11 illustrates an example of a stereoscopic image whose display on the display unit 132 is controlled by the display control unit 1353 according to the first embodiment. In FIG. 11, a case in which the nine parallax images described with reference to FIG. 10 are displayed by the display unit 132 is described as an example. In the example illustrated in FIG. 11, for example, a stereoscopic image I20 displayed by the display unit 132 looks such that the size of the "traverse direction×longitudinal direction×depth direction" is "10 cm×10 cm×10 cm." It is because the scale ratio is "1:1:0.5," but the parallax image group is generated from the virtual volume data whose three-direction ratio is "0.5:0.5:1."

As described above, even when the parallactic angle is determined in a range in which an image having no blur is displayed, the workstation 130 according to the first embodiment can cause the stereoscopic image whose the three-direction ratio is substantially the same as the three-direction ratio of the 3D subject image represented by the volume data to be displayed on the display unit 132.

Figure 12A:
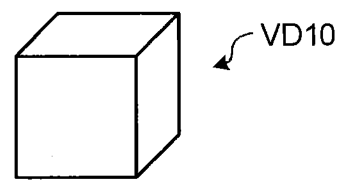
FIGS. 12A and 12B are diagrams for describing an example of a process performed by a rendering control unit according to the first embodiment.
Figure 12A:
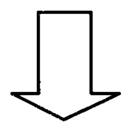
Figure 12A:
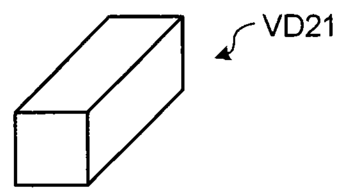
Figure 12A:
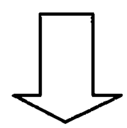
Figure 12A:
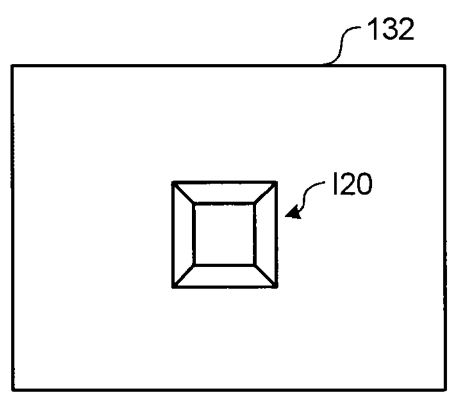
Figure 12B:
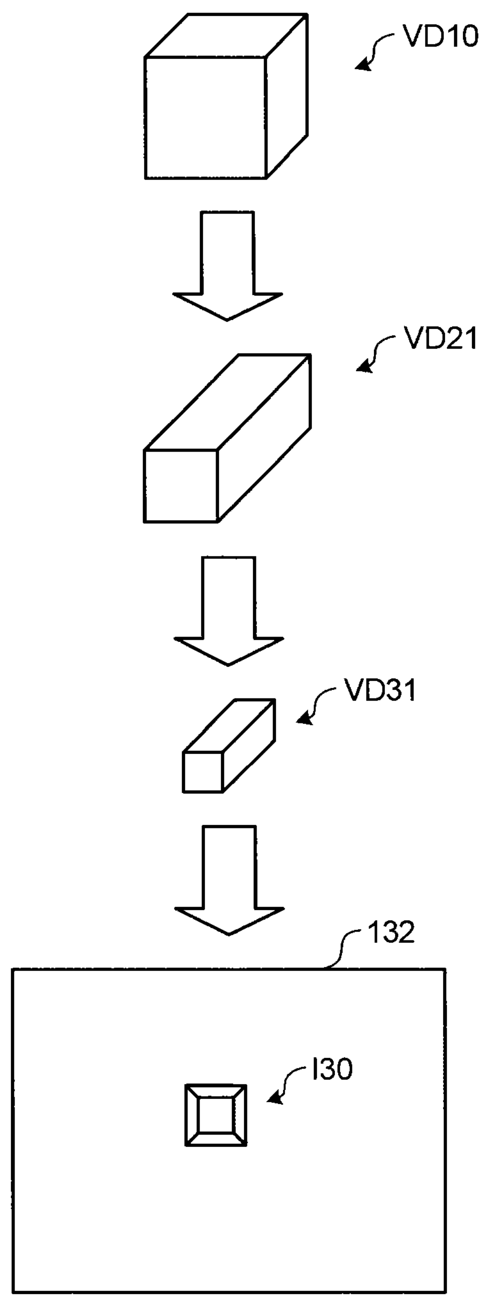

Further, the above description has been made in connection with the example in which the display size (display magnification) in the display unit 132 is "once (unmagnified)," but when the display size is not "once (unmagnified), " the rendering control unit 1352 reduces or enlarges the virtual volume data based on the display size. A concrete description will be made with reference to FIGS. 12A and 12B. FIGS. 12A and 12B are diagrams for describing an example of a process performed by the rendering control unit 1352 according to the first embodiment. FIG. 12A illustrates an example in which the display size is "once (unmagnified)," and FIG. 12B illustrates an example in which the display size is "0.5 times." The example illustrated in FIG. 12A is the same as the generation example of the virtual volume data VD21 illustrated in FIG. 10A.

As illustrated in FIG. 12B, when the display size is "0.5 times," the rendering control unit 1352 causes the rendering processing unit 136 to generate the virtual volume data VD21, similarly to when the display size is "once." Then, the rendering control unit 1352 generates virtual volume data VD31 by controlling the rendering processing unit 136 such that the sizes of the virtual volume data VD21 in the traverse direction, the longitudinal direction, and the depth direction are reduced to "0.5 times" based on the display size of "0.5 times." The rendering control unit 1352 performs the same process on the volume data at each point-of-view position as described above with reference to FIG. 10. Through this operation, as illustrated in FIG. 12B, the stereoscopic image I30 displayed by the display unit 132 becomes substantially the same in the three-direction ratio as the 3D subject image, and becomes "0.5 times" larger in the overall size than the stereoscopic image I20.

Figure 13:
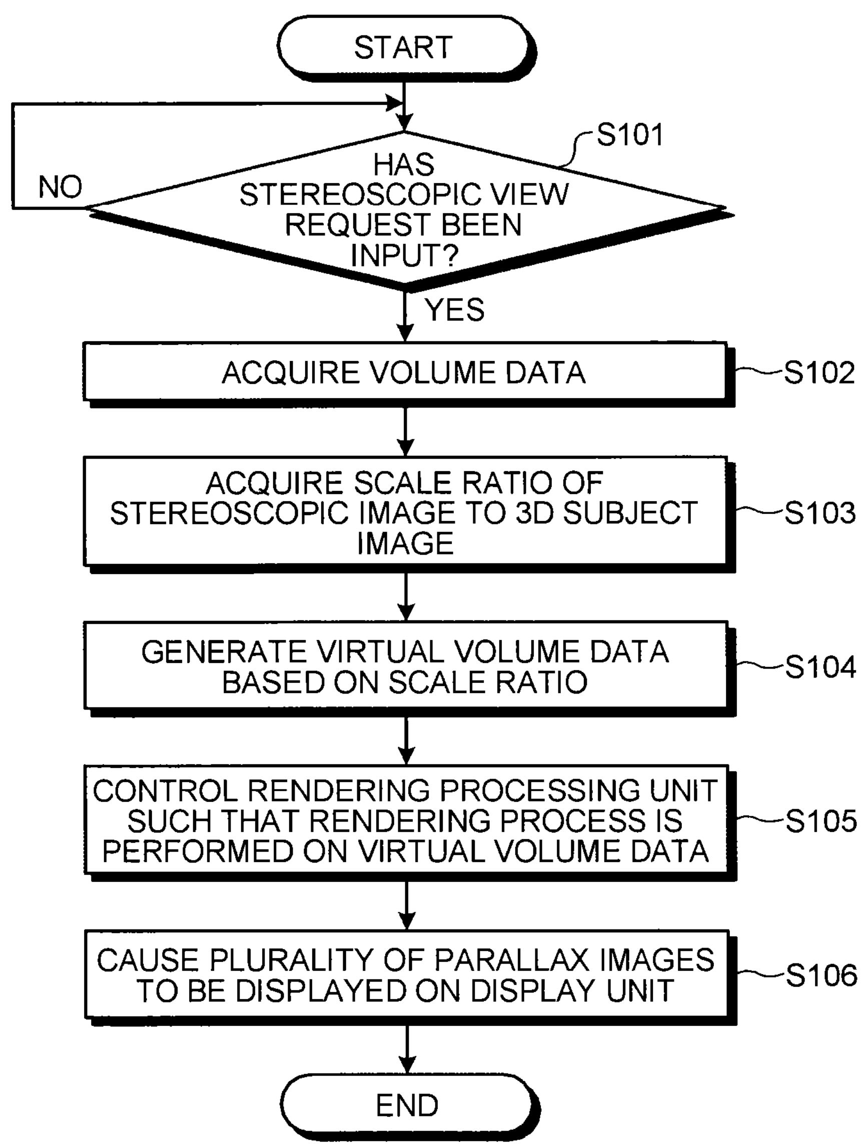
FIG. 13 is a flowchart illustrating an example of the flow of a process performed by a workstation according to the first embodiment.

Next, an example of the flow of a process performed by the workstation 130 according to the first embodiment will be described with reference to FIG. 13. FIG. 13 is a flowchart illustrating an example of the flow of a process performed by the workstation 130 according to the first embodiment.

As illustrated in FIG. 13, the control unit 135 of the workstation 130 determines whether a stereoscopic view request has been input from an observer through the input unit 131 (step S101). Here, when the stereoscopic view request has not been input (No in step S101), the workstation 130 is on standby until the stereoscopic view request is input.

However, when the stereoscopic view request has been input (Yes in step S101), the control unit 135 acquires volume data from the image storage device 120 (step S102). Subsequently, the acquiring unit 1351 acquires a scale ratio of a stereoscopic image to a 3D subject image based on the rendering condition (parallactic angle) used when the rendering process is performed on the volume data (step S103).

Subsequently, the rendering control unit 1352 generates virtual volume data by controlling the rendering processing unit 136 based on the scale ratio acquired by the acquiring unit 1351 such that the size of the volume data in each direction is reduced or enlarged (step S104). Then, the rendering control unit 1352 controls the rendering processing unit 136 such that the rendering process is performed on the virtual volume data (step S105).

Then, the display control unit 1353 causes a plurality of parallax images, which are generated by the rendering processing unit 136 under control of the rendering control unit 1352, to be displayed on the display unit 132 (step S106).

As described above, according to the first embodiment, it is possible to display a stereoscopic image having substantially the same ratio as the ratio of the sizes of a subject image in the respective directions.

Second Embodiment

The first embodiment has been described in connection with the example in which the volume data is reduced or enlarged in view of that the scale ratio is determined based on the "parallactic angle" which is the rendering condition, and thereafter the volume rendering process is performed. However, the size of the stereoscopic image, which is displayed by the display unit 132, in the depth direction may be limited to a predetermined limit value depending on a specification (performance) of the display unit 132. A second embodiment will be described in connection with an example in which volume data is reduced or enlarged also in view of a limit value of the size in the depth direction determined depending on a specification of the display unit 132 or the like.

In the following, in a stereoscopic image displayed by the display unit 132, a limit value of the size in a direction closer to the observer's point of view from the display surface of the display unit 132 is sometimes referred to as a "protruding limit amount", and a limit value of the size in a direction away from the observer's point of view from the display surface of the stereoscopic display monitor is sometimes referred to as a "depth limit amount." Further, the size obtained by adding the "protruding limit amount" and the "depth limit amount" is sometimes referred to as a "stereoscopic limit amount."

Figure 14:
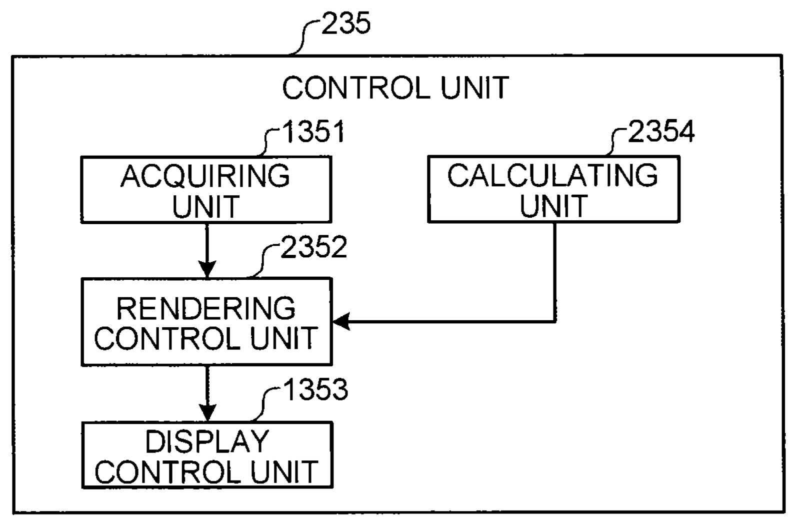
FIG. 14 is a diagram for describing a configuration example of a control unit according to a second embodiment.

First, a control unit 235 according to the second embodiment will be described with reference to FIG. 14. FIG. 14 is a diagram for describing a configuration example of the control unit 235 according to the second embodiment. The control unit 235 illustrated in FIG. 14 corresponds to the control unit 135 illustrated in FIG. 4 and is included in the workstation 130. In the following, components having the same functions as the above-described components are denoted by the same reference numerals, and thus a detailed description thereof will not be made. As illustrated in FIG. 14, the control unit 235 according to the second embodiment includes an acquiring unit 1351, a rendering control unit 2352, a display control unit 1353, and a calculating unit 2354.

The calculating unit 2354 calculates the stereoscopic limit amount which is the limit value of a stereoscopic amount based on a specification of the display unit 132. Specifically, the calculating unit 2354 calculates the protruding limit amount which is the limit value of a protruding amount displayable by the display unit 132 and the depth limit amount which is the limit value of a depth amount displayable by the display unit 132, and calculates the stereoscopic limit amount by adding the calculated protruding limit amount and the calculated depth limit amount.

In further detail, the calculating unit 2354 according to the second embodiment calculates the protruding limit amount and the depth limit amount based on a visual distance which is the distance between the display surface of the stereoscopic display monitor and the observer who observes the stereoscopic display monitor and a hardware specification of the stereoscopic display monitor. Further, the visual distance between the stereoscopic display monitor and the observer is considered to be hardly calculated unless the observer's position is specified. However, the display unit 132 or the like which is the stereoscopic display monitor is generally designed after an observation position of the stereoscopic display monitor is assumed to be a predetermined position. In this regard, the calculating unit 2354 according to the second embodiment calculates the protruding limit amount and the depth limit amount based on an "assumed visual distance" which is the distance between the observation position assumed to be a predetermined position and the display surface of the stereoscopic display monitor.

Here, examples of the protruding limit amount and the depth limit amount calculated by the calculating unit 2354 will be described. For example, the calculating unit 2354 calculates the protruding limit amount by the following Formula (1). Further, for example, the calculating unit 2354 calculates the depth limit amount by the following Formula (2). Then, the calculating unit 2354 calculates the stereoscopic limit amount by adding an absolute value of the protruding limit amount calculated by Formula (1) and an absolute value of the depth limit amount calculated by Formula (2). In the following Formulas (1) and (2), in the depth direction, the display surface of the stereoscopic display monitor is used as an original point, a direction closer to the observer's point of view from the display surface is negative, and a direction away from the observer's point of view from the display surface is positive.

$$\text{Protruding limit amount(mm)} = -\text{assumed visual distance}/\{2\times[(\text{assumed visual distance}+\text{gap})/\text{assumed visual distance}]\times(\text{sub-pixel pitch}/\text{gap})\times\text{protruding limit frequency}+1\} \quad (1)$$

$$\text{Depth limit amount(mm)} = \text{assumed visual distance}/\{2\times[(\text{assumed visual distance}+\text{gap})/\text{assumed visual distance}]\times(\text{sub-pixel pitch}/\text{gap})\times\text{protruding limit frequency}-1\} \quad (2)$$

Figure 15:
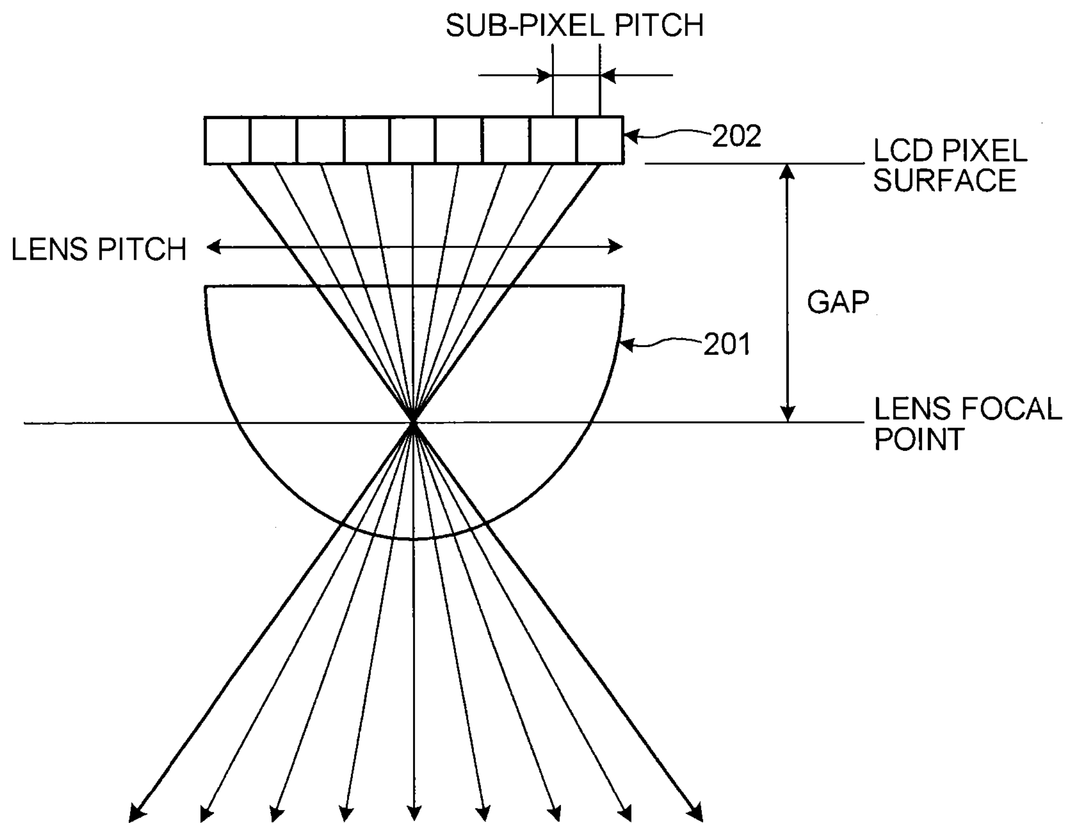
FIG. 15 is a diagram when a stereoscopic display monitor illustrated in FIG. 3 is viewed in a longitudinal direction.

Here, a "gap," "sub-pixel pitch," and the like given in Formulas (1) and (2) will be described with reference to FIG. 15. FIG. 15 is a diagram when the stereoscopic display monitor illustrated in FIG. 3 is viewed in the longitudinal direction (y axis direction). As illustrated in FIG. 15, the "gap" refers to a distance between a Liquid Crystal Display (LCD) pixel surface and a focal point of a lenticular lens 201. Further, the "sub-pixel pitch" refers to the distance between LCD pixels 202 arranged in the stereoscopic display monitor. Further, the "lens pitch" refers to the length of the LCD pixels 202 corresponding to the parallax number in the traverse direction, and is represented by "sub-pixel pitch×parallax number."

Further, the "protruding limit frequency" given in Formulas (1) and (2) uses a "cycles per radian (CPR)" as a unit, and is represented by "maximum displayable frequency×N ($0<N\leq1$)." The "maximum displayable frequency" represents the resolution on the display surface of the stereoscopic display monitor, which is represented by "visual distance/(2×lens pitch)." In further detail, the "CPR" represents the density of a beam allowable to a beam weight spread from the observer's eyes among beams emitted from the stereoscopic display monitor. In the case of the same visual distance, the "CPR" increases as the arrangement density of the lenticular lens increases, and decreases as the arrangement density of the lenticular lens decreases. In other words, when the arrangement density of the lenticular lens is the same, the "CPR" increases as the visual distance increases and decreases as the visual distance decreases. The "maximum displayable frequency" is the resolution, that is, the resolution on the display surface of the stereoscopic display monitor, which causes the "CPR" to be maximum.

Here, in Formulas (1) and (2), for example, it is assumed that the visual distance is "1000 mm," the gap is "0.5 mm," the sub-pixel pitch is "0.05 mm," and the protruding limit frequency is "300 CPR." In this case, the calculating unit 2354 calculates the protruding limit amount of "−16.4 mm" by Formula (1), and calculates the depth limit amount of "16.9 mm" by Formula (2). Here, the second decimal place is assumed to be rounded off. Then, the calculating unit 2354 calculates the stereoscopic limit amount of "33.3 mm" by adding the absolute value of the protruding limit amount and the absolute value of the depth limit amount.

Referring back to FIG. 14, the rendering control unit 2352 causes the rendering processing unit 136 to generate virtual volume data and to perform the rendering process on the virtual volume data, based on the scale ratio acquired by the acquiring unit 1351 and the stereoscopic limit amount calculated by the calculating unit 2354.

Specifically, the rendering control unit 2352 according to the second embodiment controls the rendering processing unit 136 based on the scale ratio acquired by the acquiring unit 1351 and the display size of the display unit 132 such that volume data is reduced or enlarged in a range in which the stereoscopic amount (the size in the depth direction) of the stereoscopic image does not exceed the stereoscopic limit amount calculated by the calculating unit 2354.

A process performed by the rendering control unit 2352 according to the second embodiment will be described below using several examples. The size of the 3D subject image in each direction, which will be described below, is the size when viewed from the point-of-view position (A) illustrated in FIG. 10, and the size of the stereoscopic image is also the size when viewed from the point-of-view position (A).

First, as a first example, in the display size (display magnification) of the display unit 132, the scale ratio of the acquiring unit 1351, the stereoscopic limit amount of the calculating unit 2354, and the size of "traverse direction×longitudinal direction×depth direction" of a 3D subject image represented by volume data is assumed to be the following value.

Display size: "once (unmagnified)"
Scale ratio: "1:1:0.5"
Stereoscopic limit amount: "8 cm"
3D subject image: "20 cm×20 cm×20 cm"

In the first example, for example, it is assumed that virtual volume data whose size of "traverse direction×longitudinal direction×depth direction" is "10 cm×10 cm×20 cm" is generated. In this case, the size of the stereoscopic image displayed by the display unit 132 is "10 cm×10 cm×8 cm." Since the display size is "once (unmagnified)" and the scale ratio is "1:1:0.5," the size of the stereoscopic image is considered to be "10 cm×10 cm×10 cm," but since the stereoscopic limit amount is originally "8 cm," the stereoscopic amount (the size in the depth direction) of the stereoscopic image is limited to "8 cm."

In this regard, the rendering control unit 2352 causes the rendering processing unit 136 to generate, for example, virtual volume data of "8 cm×8 cm×16 cm" so that the three-direction ratio of the stereoscopic image can be substantially the same as the three-direction ratio of the 3D subject image. The stereoscopic image displayed using the parallax image group generated from the virtual volume data becomes "8 cm×8 cm×8 cm," and thus has the same three-direction ratio as the three-direction ratio "1:1:1" of the 3D subject image. Specifically, since the display size is "once (unmagnified)" and the scale ratio is "1:1:0.5," the stereoscopic image becomes "8 cm×8 cm×8 cm." The rendering control unit 2352 may cause virtual volume data of "8 cm×8 cm×20 cm" to be generated instead of causing virtual volume data of "8 cm×8 cm×16 cm." In this case, the stereoscopic image displayed using the parallax image group generated from the virtual volume data is considered to become "8 cm×8 cm×10 cm," but since the stereoscopic limit amount is "8 cm," the stereoscopic image becomes "8 cm×8 cm×8 cm."

Subsequently, as a second example, a variety of information described above is assumed to be the following values.

Display size: "once (unmagnified)"
Scale ratio: "1:1:0.5"
Stereoscopic limit amount: "10 cm"
3D subject image: "20 cm×20 cm×20 cm"

In the second example, since the stereoscopic limit amount is "10 cm," the rendering control unit 2352 preferably generates, for example, virtual volume data of "10 cm×10 cm×20 cm" only in view of the scale ratio, similarly to the first embodiment. Through this operation, the size of the stereoscopic image displayed by the display unit 132 becomes "10 cm×10 cm×10 cm" and thus has the same three-direction ratio as the three-direction ratio "1:1:1" of the 3D subject image.

Subsequently, as a third example, a variety of information described above is assumed to be the following values.

Display size: "twice"
Scale ratio: "1:1:0.5"
Stereoscopic limit amount: "10 cm"
3D subject image: "10 cm×10 cm×10 cm"

In the third example, since the display size is "twice," the stereoscopic image displayed using the parallax image group generated from the volume data becomes "20 cm×20 cm×10 cm." In this case, the rendering control unit 2352 preferably causes the rendering processing unit 136 to generate, for example, virtual volume data of "10 cm×10 cm×20 cm" so that the three-direction ratio of the stereoscopic image can be substantially the same as the three-direction ratio of the 3D subject image. Through this operation, the size of the stereoscopic image displayed by the display unit 132 becomes "10 cm×10 cm×10 cm," and thus has the same three-direction ratio as the three-direction ratio "1:1:1" of the 3D subject image.

In the third example, in spite of that the display size is "twice," the stereoscopic image displayed by the display unit 132 has the same size as the 3D subject image. Regarding this point, the observer can select whether to give a priority to a display of a stereoscopic image having substantially the same three-direction ratio as the 3D subject image or a display of a stereoscopic image according to the display size. For example, when the observer performs an operation of giving a priority to an identity of the three-direction ratio, the rendering control unit 2352 causes the rendering processing unit 136 to generate virtual volume data of "5 cm×5 cm×10 cm" as described above. However, when the observer performs an operation of giving a priority to the display size, the rendering control unit 2352 causes the rendering processing unit 136 to generate virtual volume data of "20 cm×20 cm×20 cm." In this case, the display unit 132 displays the stereoscopic image of "20 cm×20 cm×10 cm."

Subsequently, as a fourth example, a variety of information described above is assumed to be the following values.

Display size: "once (unmagnified)"
Scale ratio: "1:1:0.5"
Stereoscopic limit amount: "8 cm"
3D subject image: "10 cm×20 cm×20 cm"

In the fourth example, the stereoscopic image displayed using the parallax image group generated from the volume data becomes "10 cm×20 cm×8 cm." In this case, the rendering control unit 2352 preferably causes the rendering processing unit 136 to generate, for example, virtual volume data of "4 cm×8 cm×16 cm." Through this operation, the size of the stereoscopic image displayed by the display unit 132 becomes “4 cm×8 cm×8 cm” and thus has the same three-direction ratio as the three-direction ratio “1:2:2” of the 3D subject image. The rendering control unit 2352 may cause virtual volume data of “4 cm×8 cm×20 cm” to be generated instead of causing virtual volume data of “4 cm×8 cm×16 cm”. Even in this case, the stereoscopic image displayed using the parallax image group generated from the virtual volume data becomes “4 cm×8 cm×8 cm.”

Subsequently, as a fifth example, a variety of information described above is assumed to be the following values.

Display size: “once (unmagnified)”

Scale ratio: “1:1:0.5”

Stereoscopic limit amount: “10 cm”

3D subject image: “10 cm×10 cm×10 cm”

In the fifth example, the stereoscopic image displayed using the parallax image group generated from the volume data becomes “10 cm×10 cm×5 cm.” In this case, the rendering control unit 2352 preferably causes the rendering processing unit 136 to generate, for example, virtual volume data of “5 cm×5 cm×10 cm.” Through this operation, the size of the stereoscopic image displayed by the display unit 132 becomes “5 cm×5 cm×5 cm” and thus has the same three-direction ratio as the three-direction ratio “1:1:1” of the 3D subject image.

Here, in the fifth example, since the stereoscopic amount (the size in the depth direction) of the stereoscopic image is “5 cm,” the stereoscopic amount is smaller than the stereoscopic limit amount “10 cm,” that is, there is room from the stereoscopic limit amount displayable by the display unit 132. In this case, the rendering control unit 2352 may cause the rendering processing unit 136 to generate virtual volume data of “10 cm×10 cm×20 cm” so that the stereoscopic amount (the size in the depth direction) of the stereoscopic image can be substantially the same as the stereoscopic limit amount. The stereoscopic image displayed using the parallax image group generated from the virtual volume data becomes “10 cm×10 cm×10 cm.” Through this operation, the rendering control unit 2352 can cause the rendering processing unit 136 to generate a parallax image group which is displayed by a maximum displayable stereoscopic amount. In other words, the rendering control unit 2352 can cause a stereoscopic image, which has substantially the same three-direction ratio as the 3D subject image to be displayed to be as large as possible on the display unit 132.

Figure 16:
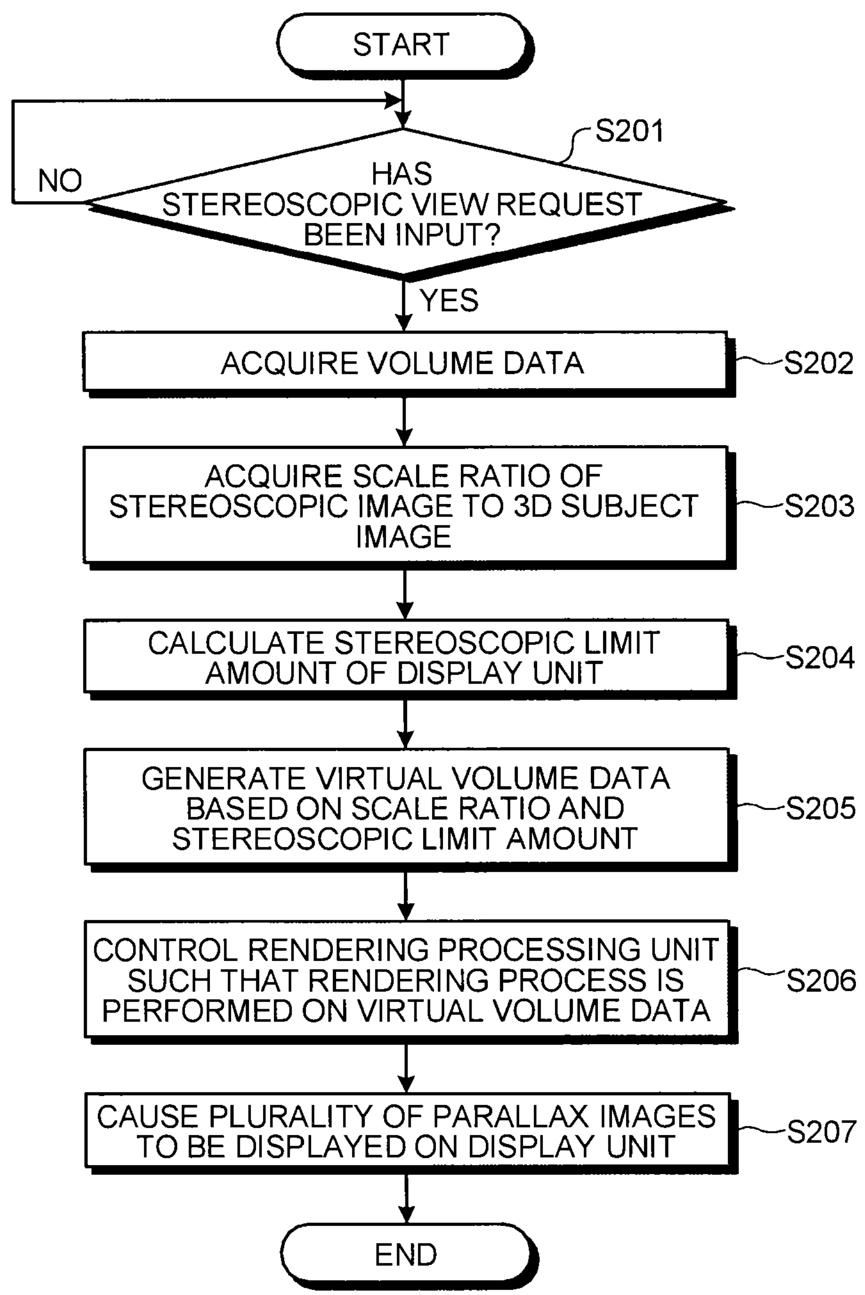
FIG. 16 is a flowchart illustrating an example of the flow of a process performed by a workstation according to the second embodiment.

Next, an example of the flow of a process performed by the workstation 130 according to the second embodiment will be described with reference to FIG. 16. FIG. 16 is a flowchart illustrating an example of the flow of a process performed by the workstation 130 according to the second embodiment.

As illustrated in FIG. 16, the control unit 235 of the workstation 130 determines whether a stereoscopic view request has been input from an observer through the input unit 131 (step S201). Here, when the stereoscopic view request has not been input (No in step S201), the workstation 130 is on standby until the stereoscopic view request is input.

However, when the stereoscopic view request has been input (Yes in step S201), the control unit 235 acquires volume data from the image storage device 120 (step S202). Subsequently, the acquiring unit 1351 acquires a scale ratio of a stereoscopic image to a 3D subject image based on the rendering condition (parallactic angle) used when the rendering process is performed on the volume data (step S203).

Subsequently, the calculating unit 2354 calculates a stereoscopic limit amount based on a specification of the display unit 132 (step S204). For example, the calculating unit 2354 calculates the stereoscopic limit amount using Formulas (1) and (2).

Subsequently, the rendering control unit 2352 controls the rendering processing unit 136 such that virtual volume data is generated, based on the scale ratio acquired by the acquiring unit 1351 and the stereoscopic limit amount calculated by the calculating unit 2354 (step S205). Then, the rendering control unit 2352 controls the rendering processing unit 136 such that the rendering process is performed on the virtual volume data (step S206).

Then, the display control unit 1353 causes a plurality of parallax images, which are generated by the rendering processing unit 136 under control of the rendering control unit 2352, to be displayed on the display unit 132 (step S207).

As described above, according to the second embodiment, it is possible to display a stereoscopic image having substantially the same ratio as the ratio of the sizes of a subject image in the respective directions.

The first and second embodiments may be embodied by other embodiments. Therefore, the other embodiments will be described below.

Parallel Display

Figure 11:
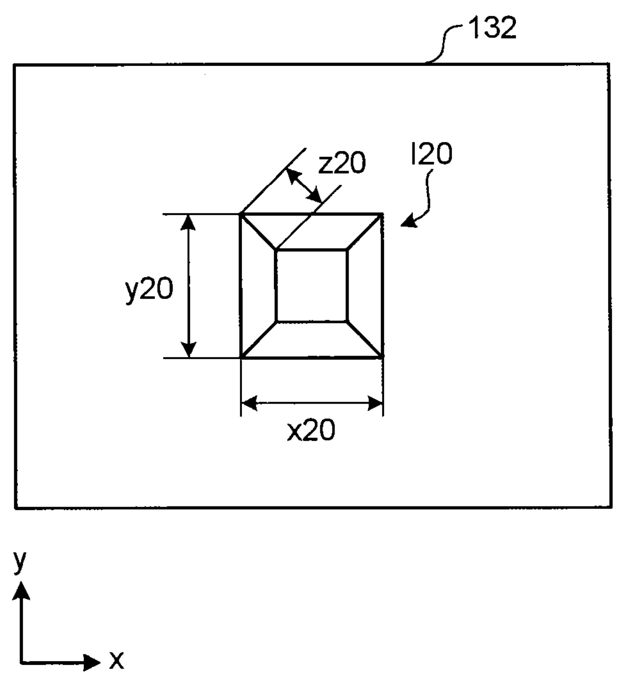
FIG. 11 is a diagram illustrating an example of a stereoscopic image whose display on a display unit is controlled by a display control unit according to the first embodiment.
Figure 17:
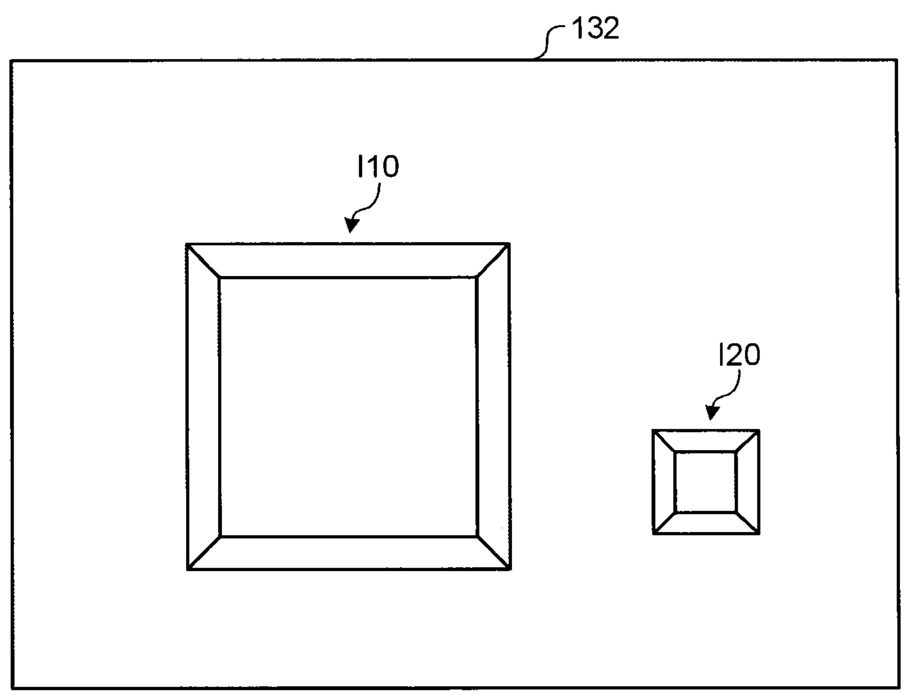
FIG. 17 is a diagram illustrating an example of a stereoscopic image parallel-displayed by a display unit.

In the above embodiments, the workstation 130 changes the size of volume data based on the parallactic angle or the stereoscopic limit amount, and thus a stereoscopic image displayed by the display unit 132 may be reduced (see FIG. 11). Thus, the display control unit 1353 of the workstation 130 may cause a parallax image group generated from virtual volume data and a parallax image group generated from volume data, which has not been reduced by the rendering control unit 2352 to be parallel-displayed on the display unit 132. FIG. 17 illustrates an example of a parallel-displayed stereoscopic image. FIG. 17 is a diagram illustrating an example of a stereoscopic image parallel-displayed by the display unit 132.

In the example illustrated in FIG. 17, the display unit 132 displays the stereoscopic image I10 illustrated in FIG. 8 and the stereoscopic image I20 illustrated in FIG. 11. In other words, the display unit 132 displays a parallax image group generated from the volume data VD10 illustrated in FIG. 8 and a parallax image group generated from the virtual volume data VD21 and VD22, and the like illustrated in FIG. 10. Through this operation, the observer can minutely check a subject image with reference to the stereoscopic image I10 and understand a sense of distance of a subject image with reference to the stereoscopic image I20.

Scale Ratio

Further, in the above embodiments, the acquiring unit 1351 acquires the ratio of the scale in the traverse direction, the scale in the longitudinal direction, and the scale in the depth direction as the scale ratio. However, the acquiring unit 1351 may not acquire the ratio of the scales in the three directions. For example, the acquiring unit 1351 may acquire the ratio of the scale in the traverse direction and the scale in the depth direction as the scale ratio or may acquire the ratio of the scale in the longitudinal direction and the scale in the depth direction as the scale ratio.

Display Size (Display Magnification)

Further, in the above embodiments, the acquiring unit 1351 acquires the scale ratio, and the rendering control unit 1352 causes the rendering processing unit 136 to generate virtual volume data based on the scale ratio. However, the acquiring unit 1351 may not acquire the scale ratio. Specifically, the acquiring unit 1351 may acquire the scale of the stereoscopic image, which is assumed to be displayed by the display unit 132, to the 3D subject image in each of the traverse direction (x direction), the longitudinal direction (y direction), and the depth direction (z direction). The rendering control unit 1352 may control the rendering processing unit 136 such that virtual volume data is generated so that the scale, in each direction, acquired by the acquiring unit 1351 can be substantially the same as a display size (display magnification) designated by a system.

For example, the display size (display magnification) is assumed to be set to "0.5." The acquiring unit 1351 is assumed to acquire the scale "0.5" in the traverse direction (x direction), the scale "0.4" in the longitudinal direction (y direction), and the scale "0.1" in the depth direction (z direction). Here, since the display size (display magnification) is "0.5," the scale in each direction is desirably "0.5." Therefore, the rendering control unit 1352 controls the rendering processing unit 136 such that volume data is reduced or enlarged so that the scale in each direction acquired by the acquiring unit 1351 can be substantially the same as the display size "0.5." Through this operation, the workstation 130 can cause a stereoscopic image, which has substantially the same three-direction ratio as the 3D subject image, to be displayed on the display unit 132.

Head Tracking

Further, in the second embodiment, as expressed in Formulas (1) and (2), the calculating unit 2354 calculates the stereoscopic limit amount using the assumed visual distance in which a predetermined position is assumed as a visual distance. However, the calculating unit 2354 may measure a visual distance between an observation position and the display surface of the stereoscopic display monitor using a technique such as head tracking. In this case, the calculating unit 2354 calculates the stereoscopic limit amount using the visual distance measured by head tracking or the like instead of the assumed visual distance in Formulas (1) and (2).

Processing Entity

Further, in the first and second embodiments, the workstation 130 causes a parallax image group generated from virtual volume data to be displayed on the display unit 132. However, an embodiment is not limited to this example. For example, the workstation 130 may store a parallax image group generated from virtual volume data in the image storage device 120. In this case, the terminal device 140 acquires the parallax image group generated by the workstation 130 from the image storage device 120, and causes the acquired parallax image group to be displayed on the stereoscopic display monitor included in the terminal device 140. Through this operation, the terminal device 140 can display stereoscopic images illustrated in FIGS. 11 and 17 and the like. Further, the calculating unit 2354 of the workstation 130 can calculate the stereoscopic limit amount by acquiring a specification of the stereoscopic display monitor from the terminal device 140.

Further, in the above embodiments, the medical image diagnostic device 110 may be integrated with the workstation 130. In other words, the medical image diagnostic device 110 may have a function equivalent to the control unit 135 or the control unit 235, generate virtual volume data, and generate a parallax image group based on the generated virtual volume data.

Further, the terminal device 140 may have a function equivalent to the control unit 135 or the control unit 235, acquire volume data from the medical image diagnostic device 110 or the image storage device 120, generate virtual volume data based on the acquired volume data, and generate a parallax image group based on the virtual volume data.

Further, in the above embodiments, the rendering processing unit 136 generates virtual volume data under control of the rendering control unit 1352. However, virtual volume data may be generated by a processing unit other than the rendering processing unit 136. For example, the rendering control unit 1352 may have a function equivalent to the 3D geometric transform processing unit **1362*b*** and generate virtual volume data.

Parallax Image

Further, the above embodiments have been described in connection with the example in which the parallax image group including nine parallax images is generated, but an embodiment is not limited to this example. For example, the rendering control unit 1352 or the rendering control unit 2352 of the workstation 130 may control the rendering processing unit 136 such that a parallax image group including two parallax images is generated. Further, in the above embodiments, volume data which is medical image data has been described as an example, but the above embodiments may be applied to a case in which volume data other than medical image data is used.

Third Embodiment

Next, a third embodiment will be described in connection with an example in which a stereoscopic image having substantially the same ratio as the ratio of the sizes of a subject image in the respective directions is displayed, and then a scale to associate volume data with a stereoscopic image is displayed.

Further, in the third embodiment, a coordinate system of volume data is represented using coordinates of three orthogonal axes of (x, y, z). Further, a horizontal direction in actual space coordinates is referred to as an x direction. Further, a vertical direction in the actual space coordinates is used as a y direction. Further, a direction vertical to an xy plane in the actual space coordinates, specifically, a direction corresponding to the "depth direction" is referred to as a z direction. In other words, a positive direction of the z direction is the "depth direction," and a negative direction of the z direction is a "protruding direction." Further, in the third embodiment, a coordinate system of a stereoscopic image space is represented by using coordinates of three orthogonal axes of (X, Y, Z). Further, a horizontal direction (a traverse direction of a display surface) in stereoscopic image space coordinates is referred to as an X direction. Further, a vertical direction (a longitudinal direction of the display surface) in the stereoscopic image space coordinates is referred to as a Y direction. Further, a direction corresponding to the "depth direction" in the stereoscopic image space coordinates is referred to as a Z direction. In other words, a positive direction of the Z direction is the "depth direction," and a negative direction of the Z direction is a "protruding direction."

Figure 18:
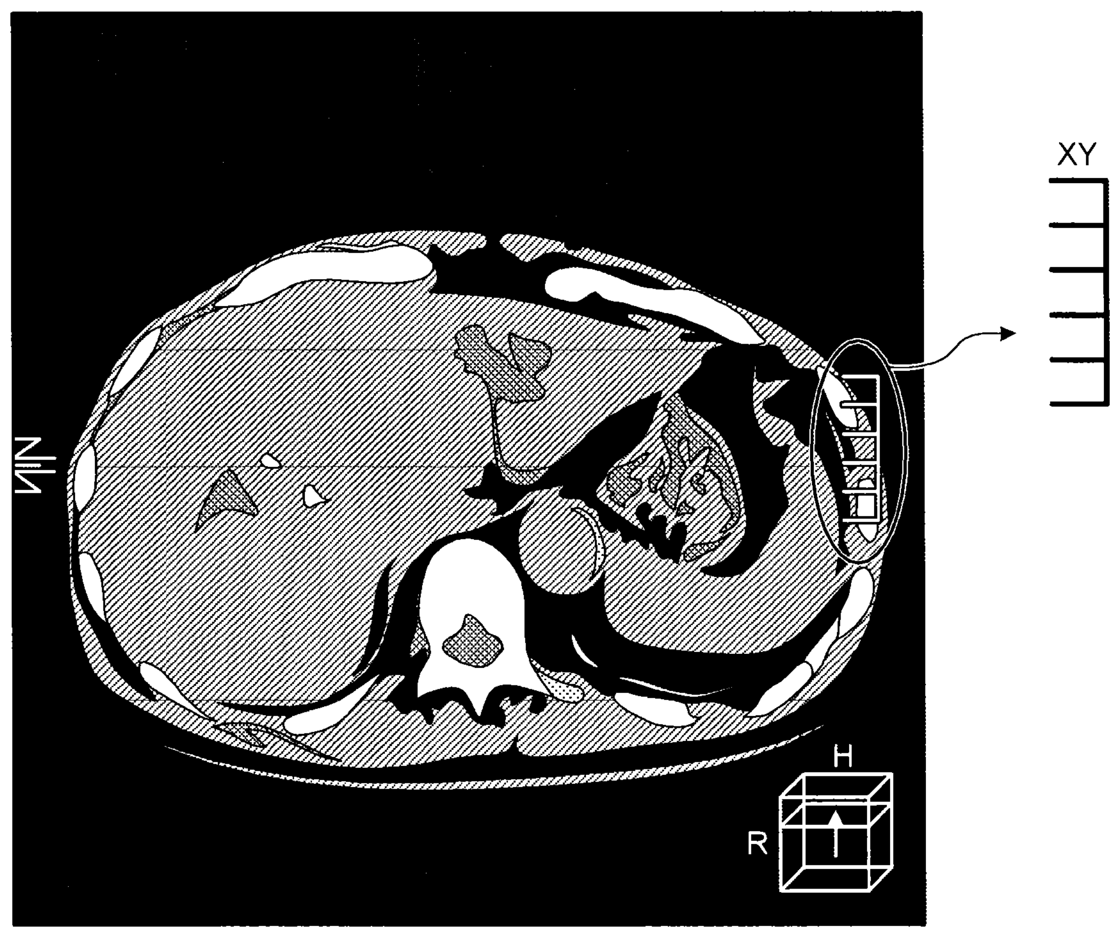
FIG. 18 is a diagram for describing a scale in a related art.

In the related art, when a 2D image obtained by cutting volume data by a cross section is two-dimensionally displayed on a general-purpose monitor, a scale in an XY direction to associate the 2D image with an actual space of a shooting portion of the volume data is displayed. The scale in the XY direction is obtained by converting the lengths of the 2D image displayed on the monitor in the traverse direction and the longitudinal direction to the lengths in the actual space corresponding to the 2D image. FIG. 18 is a diagram for describing the scale in the related art.

For example, as illustrated in FIG. 18, the general-purpose monitor displays the scale in the XY direction to associate with an axial image obtained by cutting volume data generated by an X-ray CT device by an axial plane with an actual space together with the axial image. By referring to the scale in the XY direction, the observer of the general-purpose monitor (for example, a radiologist) can roughly understand the size of an area of interest, which is represented in the axial image, in the XY direction.

Meanwhile, the stereoscopic image is stereoscopically viewed in the stereoscopic image space by the observer as described above. However, for example, the observer of the stereoscopic display monitor such as a nine-parallax monitor hardly understands the size in the stereoscopically viewed stereoscopic image space, particularly, the size in the Z direction with reference to the scale in the XY direction.

Figure 19:
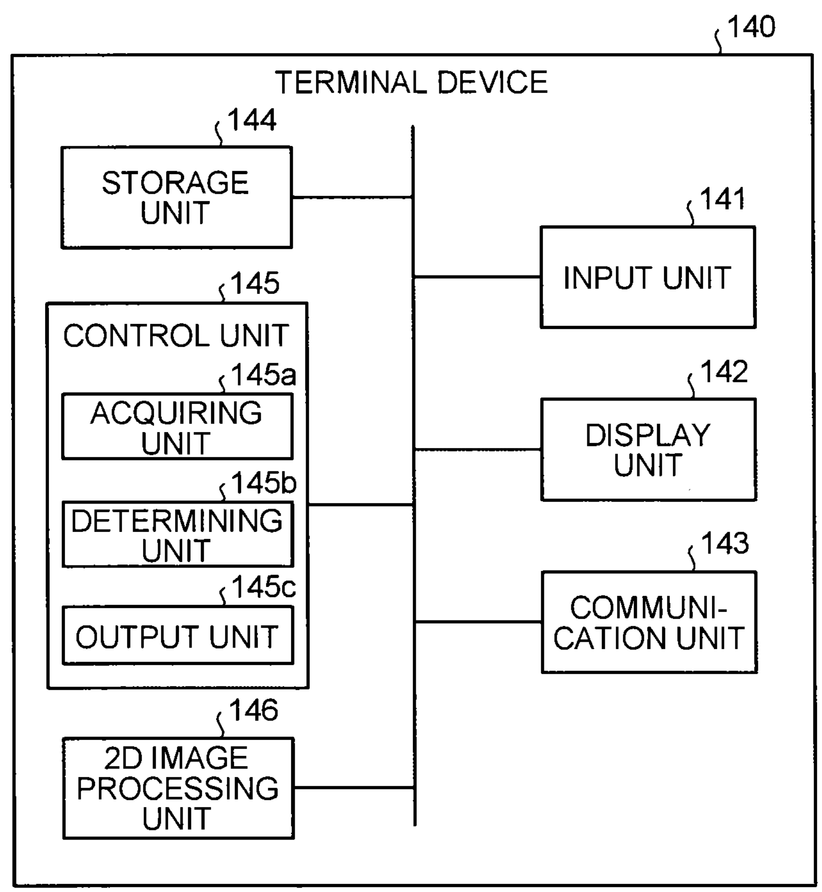
FIG. 19 is a diagram for describing a configuration example of a terminal device according to a third embodiment.

In this regard, the terminal device 140 according to the third embodiment displays a scale to associate an image stereoscopically viewed to the observer through a monitor with a stereoscopic view function with an actual space. The terminal device 140 according to the third embodiment will be described in detail with reference to FIG. 19. FIG. 19 is a diagram for describing a configuration example of the terminal device 140 according to the third embodiment.

The terminal device 140 illustrated in FIG. 19 is a device that allows a doctor or a laboratory technician who works in the hospital to observe a medical image, and acquires a parallax image group (2D output image) generated by the rendering processing unit 136 from the image storage device 120 or the workstation 130. As illustrated in FIG. 19, the terminal device 140 includes an input unit 141, a display unit 142, a communication unit 143, a storage unit 144, a control unit 145, and a 2D image processing unit 146.

The input unit 141 includes a mouse, a keyboard, a trackball, or the like, and receives various operations which an operator has input on the terminal device 140. Specifically, the input unit 141 according to the third embodiment receives the stereoscopic view request from the operator. For example, the input unit 141 receives an input of the patient ID, the inspection ID, the device ID, the series ID, or the like which is used to designate volume data desired to be displayed for the operator's interpretation as the stereoscopic view request.

The display unit 142 includes a liquid crystal panel or the like as a stereoscopic display monitor, and displays a variety of information. Specifically, the display unit 142 according to the third embodiment displays a Graphical User Interface (GUI) for receiving various operations from the operator, a stereoscopic image, or the like. For example, the display unit 142 includes a two-parallax monitor or a nine-parallax monitor. In the following, the description will proceed in connection with the example in which the display unit 142 includes the nine-parallax monitor.

The communication unit 143 includes a Network Interface Card (NIC) or the like, and performs communication with another device. For example, the communication unit 143 according to the third embodiment transmits information related to the stereoscopic view request received through the input unit 141 to the image storage device 120. Further, the communication unit 143 according to the third embodiment receives a parallax image group or the like transmitted from the image storage device 120 or the workstation 130 according to the stereoscopic view request.

The storage unit 144 includes a hard disk, a semiconductor memory device, or the like, and stores a variety of information. Specifically, the storage unit 144 according to the third embodiment stores the parallax image group or the like acquired from the image storage device 120 or the workstation 130 through the communication unit 143. Further, the storage unit 144 further stores supplementary information (a parallax number, the resolution, or the like) of the parallax image group acquired from the image storage device 120 or the workstation 130 through the communication unit 143.

The control unit 145 includes an electronic circuit such as a Central Processing Unit (CPU), or a Micro Processing Unit (MPU), or an integrated circuit (IC) such as an Application Specific Integrated Circuit (ASIC) or a Field Programmable Gate Array (FPGA). The control unit 135 controls the terminal device 140 in general.

For example, the control unit 145 controls transmission/reception of a display request to/from the image storage device 120, which is performed through the communication unit 143 and transmission/reception of the parallax image group or the like to/from the image storage device 120 or the workstation 130, which is performed through the communication unit 143. Further, for example, the control unit 145 controls an operation of storing a parallax image group or the like in the storage unit 144 or an operation of reading the parallax image group or the like from the storage unit 144.

Further, the control unit 145 according to the third embodiment controls a display of a GUI or a display of a parallax image group on the display unit 142. The control unit 145 according to the third embodiment converts the parallax image group into an interim image arranged in a predetermined format (for example, a lattice form), and causes the interim image to be displayed on the display unit 142 which is the nine-parallax monitor. Further, the control unit 145 according to the third embodiment controls image processing performed by the 2D image processing unit 146.

The control unit 145 includes an acquiring unit 145*a*, a determining unit 145*b*, and an output unit 145*c*. A process performed by the acquiring unit 145*a*, the determining unit 145*b*, and the output unit 145*c* will be described later.

The 2D image processing unit 146 has the same function as the 2D image processing unit 1363 described with reference to FIG. 5. In other words, the 2D image processing unit 146 can cause the display unit 142 to generate a 2D output image by generating an overlay and superimposing the overlay on a parallax image group, which serves as an underlay, generated by the 3D image processing unit 1362.

Further, as described above, the rendering processing unit 136 generates a parallax image group based on volume data under control of the control unit 135. Further, the terminal device 140 acquires the parallax image group and causes the acquired parallax image group to be displayed on the display unit 142. Through this operation, a doctor or a laboratory technician who is the operator of the terminal device 140 can view a stereoscopically viewable medical image in a state in which a variety of information (a scale, a patient name, an inspection item, and the like) is represented.

The control unit 145 of the terminal device 140 according to the third embodiment implements a display of the scale to associate an image, stereoscopically viewed to the observer through the monitor with a stereoscopic view function, with an actual space through the process performed by the acquiring unit 145*a*, the determining unit 145*b*, and the output unit 145*c*. Various processes will be described below as the process performed by the acquiring unit 145*a*, the determining unit 145*b*, and the output unit 145*c*.

Further, the process performed by the acquiring unit 145*a*, the determining unit 145*b*, and the output unit 145*c* is executed after the nine-parallax image is transferred to the control unit 145. In other words, the workstation 130 acquires volume data designated by the operator of the terminal device 140 from the image storage device 120, and generates a nine-parallax image, which is a parallax image group to be output to the display unit 142 which is the nine-parallax monitor, based on the acquired volume data. For example, the rendering processing unit 136 generates the nine-parallax image based on the rendering condition (the parallax number, the parallactic angle, the projection method, point-of-view position information, and the like) input by the operator of the terminal device 140. Then, the control unit 135 controls the communication unit 133 such that the nine-parallax image generated by the rendering processing unit 136 is transmitted to the terminal device 140. The communication unit 143 of the terminal device 140 transfers the received nine-parallax image to the control unit 145.

The acquiring unit 145*a* acquires correspondence information to associate coordinates of the stereoscopic image space with the actual space based on the display size of the nine-parallax image to be displayed on the display unit 142. Specifically, the acquiring unit 145*a* acquires correspondence information in the XY direction based on the display size. For example, the display size is acquired when the operator of the terminal device 140 inputs the display size together with the rendering condition.

It is assumed that the volume data is configured with voxels of "500×500×500," and one voxel has the size of "0.5 mm×0.5 mm×0.5 mm."

In this case, in an xy plane of the volume data, 10 voxels correspond to 5 mm. Here, when the display size is "1 voxel:1.0 mm," the acquiring unit 145*a* acquires correspondence information representing that an XY plane is "10 pixels:10 mm."

Here, the terminal device 140 according to the third embodiment displays a parallax image group generated by the workstation 130 described in the first or second embodiment and thus can display a stereoscopic image having substantially the same as the ratio of the sizes of a subject image in the respective directions. In other words, since the correspondence information in the XY direction is the same as the correspondence information in the Z direction, the acquiring unit 145*a* acquires correspondence information representing "10 pixels:10 mm" on the XYZ direction. Through this operation, the determining unit 145*b* determines "10 pixels:10 mm" as the scale in the XYZ direction.

The output unit 145*c* performs control such that the nine-parallax image group and the scale are output by the display unit 142. Specifically, the output unit 145*c* controls the 2D image processing unit 146 such that an overlay of the scale is generated, and then a 2D output image in which the generated overlay is superimposed on each of the underlays (nine parallax images).

Figure 20:
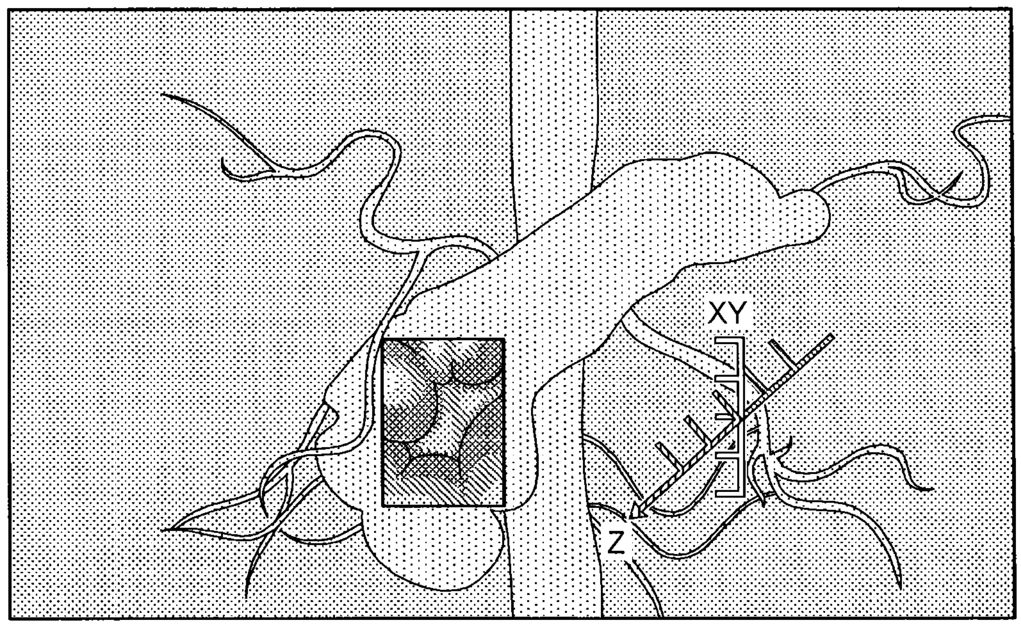
FIG. 20 is a diagram for describing an example of a display of a scale in a Z direction.

Then, the output unit 145*c* converts nine 2D output images generated by the 2D image processing unit 146, which configure the nine-parallax image, into an interim image, and outputs the interim image to the display unit 142. Through this operation, the display unit 142 displays the stereoscopic image together with the scale in the XYZ direction in a superimposed manner. FIG. 20 is a diagram for describing an example of a display of the scale in the Z direction.

In the example illustrated in FIG. 20, the scale in the Z direction in which the scale of the display surface in the protruding direction is the same as the scale in the depth direction is displayed, in a superimposed manner, in an oblique direction in order to give a stereoscopic effect to the scale in the XY direction. By referring to the scale in the Z direction, for example, the operator (observer) of the terminal device 140 can understand the size in the protruding direction of an area (see the inside of a black frame in FIG. 20) protruding from the display surface in the stereoscopic image space. Here, in the example illustrated in FIG. 20, the scale in the Z direction in which the protruding direction is a positive direction is displayed.

The scale can be moved according to the observer's request. For example, let us assume that the observer clicks the position of the scale using the mouse of the input unit 141 and then moves the mouse in the clicked state. In this case, the control unit 145 transmits an instruction to reproduce an overlay in which the position of the scale has been moved to the 2D image processing unit 146. Through this operation, the display unit 142 can display the stereoscopic image in which the position of the scale is moved according to the observer's mouse operation.

Figure 21:
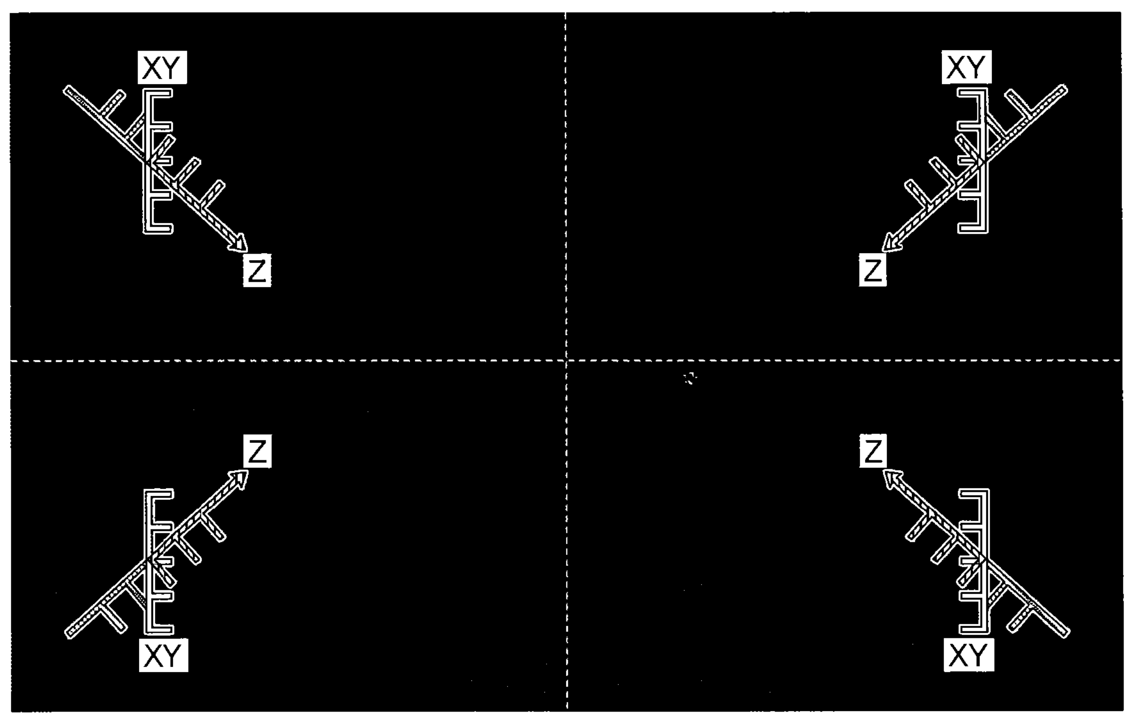
FIG. 21 is a diagram for describing an example of display control of a scale in a Z direction with the movement.

Further, the output unit 145*c* performs control such that a direction of a line segment configuring the scale is changed according to the position at which the scale is superimposed on the stereoscopic image. FIG. 21 is a diagram for describing an example of display control of the scale in the Z direction with the movement.

For example, as illustrated in FIG. 21, when the position of the scale is moved to the lower right of the display surface, the output unit 145*c* causes the 2D image processing unit 146 to generate an overlay in which the scale in the Z direction is represented by a line segment in a direction from the lower right toward the upper left. Further, as illustrated in FIG. 21, when the position of the scale is moved to the upper right of the display surface, the output unit 145*c* causes the 2D image processing unit 146 to generate an overlay in which the scale in the Z direction is represented by a line segment in a direction from the upper right toward the lower left.

Further, as illustrated in FIG. 21, when the position of the scale is moved to the lower left of the display surface, the output unit 145*c* causes the 2D image processing unit 146 to generate an overlay in which the scale in the Z direction is represented by a line segment in a direction from the lower left toward the upper right. Further, as illustrated in FIG. 21, when the position of the scale is moved to the upper left of the display surface, the output unit 145*c* causes the 2D image processing unit 146 to generate an overlay in which the scale in the Z direction is represented by a line segment in a direction from the upper left toward the lower right.

Through this control, the observer can refer to the scale without any uncomfortable feeling on a stereoscopic effect felt by the observer, particularly, a protruding feeling.

As described above, in the third embodiment, the scale in the Z direction can be displayed. Further, in the third embodiment, the terminal device 140 displays the parallax image group generated by the workstation 130 described in the first or second embodiment and thus can display a stereoscopic image having substantially the same as the ratio of the sizes of a subject image in the respective directions. In other words, the terminal device 140 can use the scale in the XY direction as the scale in the Z direction. As a result, in the third embodiment, the scale to associate an image stereoscopically viewed to the observer through the monitor with a stereoscopic view function with the actual space can be displayed, and thus the observer can roughly understand the size of an area of interest at which the observer looks.

The third embodiment can be embodied by other embodiments. Therefore, the other embodiments will be described below. FIGS. 22A to 22E, 23, and 24A to 24C are diagrams for describing modifications of the third embodiment.

Regarding Scale

Figure 22A:
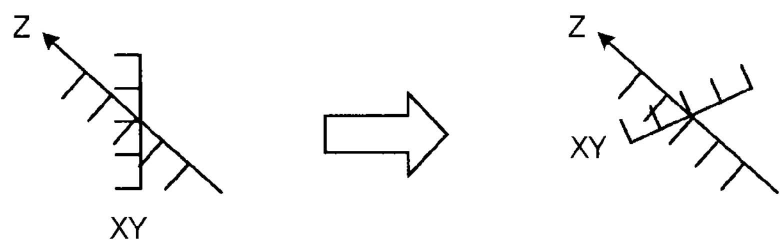
FIGS. 22A to 22E, 23, and 24A to 24C are diagrams for describing modifications of the third embodiment.

The third embodiment has been described in connection with the example in which the scale in the XY direction representing the scales in the X direction and the Y direction is fixed to the longitudinal direction of the display surface. However, the scale in the XY direction may be rotationally moved according to the operator (observer)'s mouse operation, for example, as illustrated in FIG. 22A.

Figure 22B:
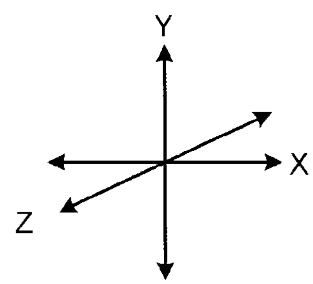

Further, the third embodiment has been described in connection with the example in which the scales in the X direction and the Y direction is unified into the scale in the XY direction. However, the scale in the XY direction may be divided into the scales in the X direction and the Y direction, for example, as illustrated in FIG. 22B.

Figure 22C:
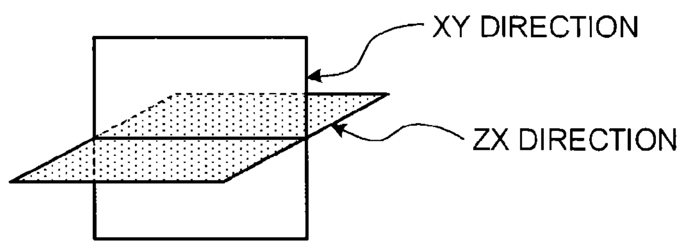
Figure 22D:
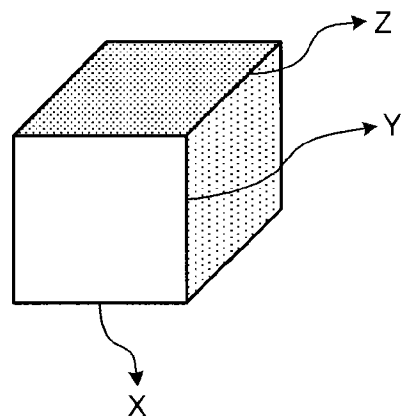
Figure 22E:
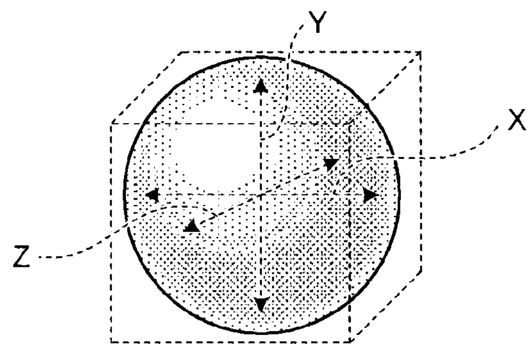

Further, the scale is not limited to one configured with a line segment described in the third embodiment. For example, the scale may be configured with a plane representing the scale in the XY direction and a plane representing the scale in the ZX direction as illustrated in FIG. 22C. Further, for example, the scale may be configured with a rectangular parallelepiped collectively representing the scale in the XYZ direction as illustrated in FIG. 22D. Further, for example, the scale may be configured with a spherical body collectively representing the scale in the XYZ direction as illustrated in FIG. 22E. However, when the scales illustrated in FIGS. 22C to 22E are displayed, it is desirable to perform a process of setting the opacity of the scale to, for example, "50%" in order to avoid a reduction in visibility of a stereoscopic image.

Further, the determining unit 145*b* may determine a grid line used to divide a stereoscopic image space in the form of a grid as the scale according to correspondence information. In other words, the scale may be a scale using a grid line as in an example illustrated in FIG. 23. In the example illustrated in FIG. 23, grid lines in the X direction, the Y direction, and the Z direction are arranged at equal intervals.

As described above, since the entire stereoscopic image space is displayed using the grid lines in the X direction, the Y direction, and the Z direction as the scale, the observer can generally understand the size of the stereoscopic image in the actual space. Further, since the entire stereoscopic image space is displayed using the grid line as the scale, the observer can more stereoscopically view the stereoscopic image.

Furthermore, the determining unit 145*b* may convert information of an axis used as a scale according to the correspondence information from a coordinate axis in a stereoscopic image space into a coordinate axis in a volume data space. In other words, the determining unit 145*b* may perform a process of converting the scale in the stereoscopic image space to the scale in the volume data space. In this case, the acquiring unit 145*a* acquires information related to the coordinate axis in the volume data space, for example, from supplementary information associated with volume data in the image storage device 120.

Figure 24A:
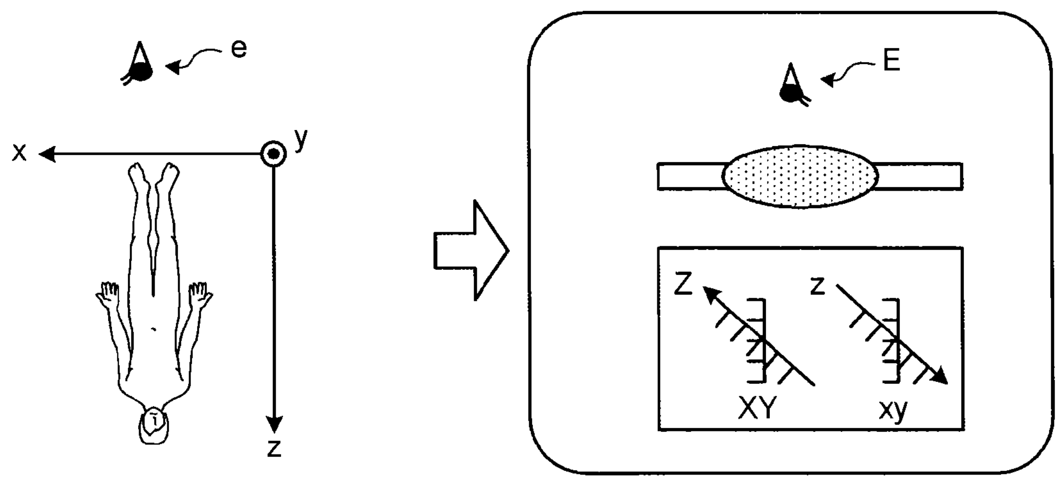
Figure 24B:
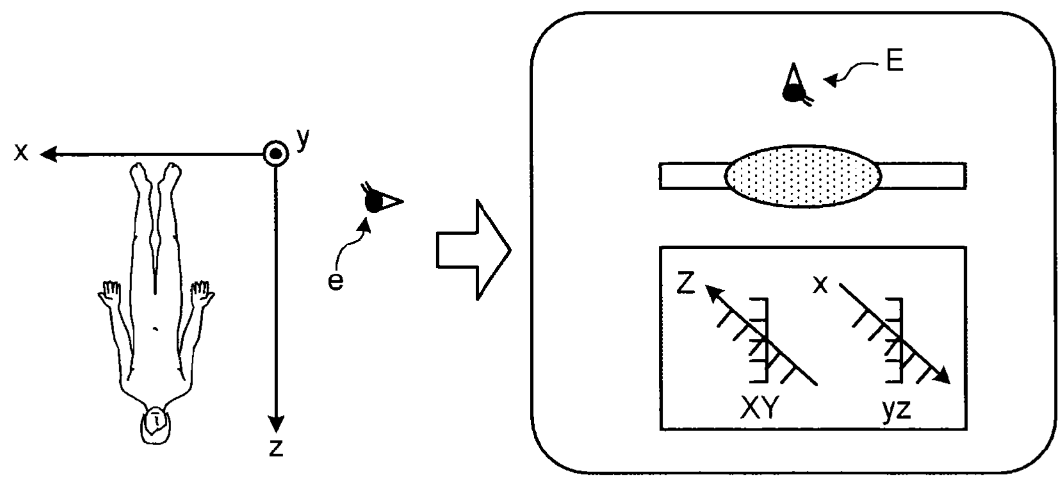

For example, as illustrated in FIGS. 24A and 24B, the acquiring unit 145*a* may acquire information representing that a direction from the foot toward the head is a positive z direction in the volume data space corresponding to the actual space, a direction from the right arm to the left arm is a positive x direction, and a direction from a back side toward a ventral side is a positive y direction from a subject's posture at the time of shooting.

Here, as illustrated in FIG. 24A, it is assumed that a line-of-sight direction from a point of view e at the time of the rendering process, which is acquired by the acquiring unit 145*a*, was a direction according to the z direction from the negative direction toward the positive direction. In this case, as described above, the determining unit 145*b* determines the scales in the XY direction and the Z direction in the stereoscopic image space (see FIG. 24A). Further, the determining unit 145*b* determines the scales in the xy direction and the z direction as the output scales, as illustrated in FIG. 24A, on the basis of that the scale in the XY direction corresponds to the scale in the xy direction and the scale in the Z direction corresponds to the scale in the z direction. Here, the determining unit 145*b* sets a direction of an arrow in the z direction to be opposite to a direction of an arrow in the Z direction, as illustrated in FIG. 24A, on the basis of that the depth direction of the stereoscopic image recognized from the observer's point of view E corresponds to the positive z direction.

Further, as illustrated in FIG. 24B, it is assumed that the line-of-sight direction from the point of view e at the time of the rendering process, which is acquired by the acquiring unit 145*a*, was a direction according to the x direction from the negative direction toward the positive direction. In this case, as described above, the determining unit 145*b* determines the scales in the XY direction and the Z direction in the stereoscopic image space (see FIG. 24B). Further, the determining unit 145*b* determines the scales in the yz direction and the x direction as the output scales, as illustrated in FIG. 24B, on the basis of that the scale in the XY direction corresponds to the scale in the yz direction and the scale in the Z direction corresponds to the scale in the x direction. Here, the determining unit 145*b* sets a direction of an arrow in the x direction to be opposite to a direction of an arrow in the Z direction, as illustrated in FIG. 24B, on the basis of that the depth direction of the stereoscopic image recognized from the observer's point of view E corresponds to the positive x direction.

Figure 24C:
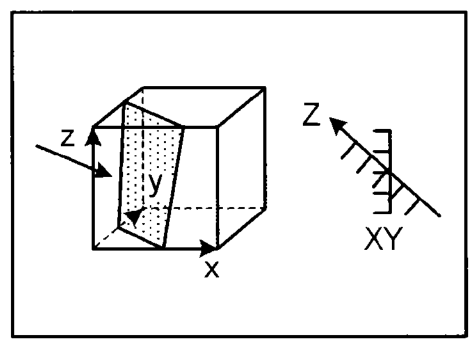

Here, as illustrated in FIGS. 24A and 24B, when the line-of-sight direction from the point of view e at the time of the rendering process is not a direction that directly faces the xy plane, the yz plane, nor the zx plane, it is not appropriate to use a symbol of xyz in a scale (hereinafter, referred to as a "V scale") in the volume data space. In this case, as illustrated in FIG. 24C, the determining unit 145*b* may cause the 2D image processing unit 146 to generate an image in which the line-of-sight direction at the time of rendering and the reference surface at the time of shooting are superimposed on a diagram schematically illustrating volume data by a cubic shape, and use the scale of the image and the scale in the XY direction and the Z direction as the V scale.

By performing this process, the observer can easily discern a direction from which volume data is observed in the volume data space when observing the stereoscopic image through the stereoscopic display monitor. Further, the above description has been made in connection with the example in which the scale in the volume data space is determined for an output together with the scale in the stereoscopic image space. However, only the scale in the volume data space may be determined for an output.

Figure 23:
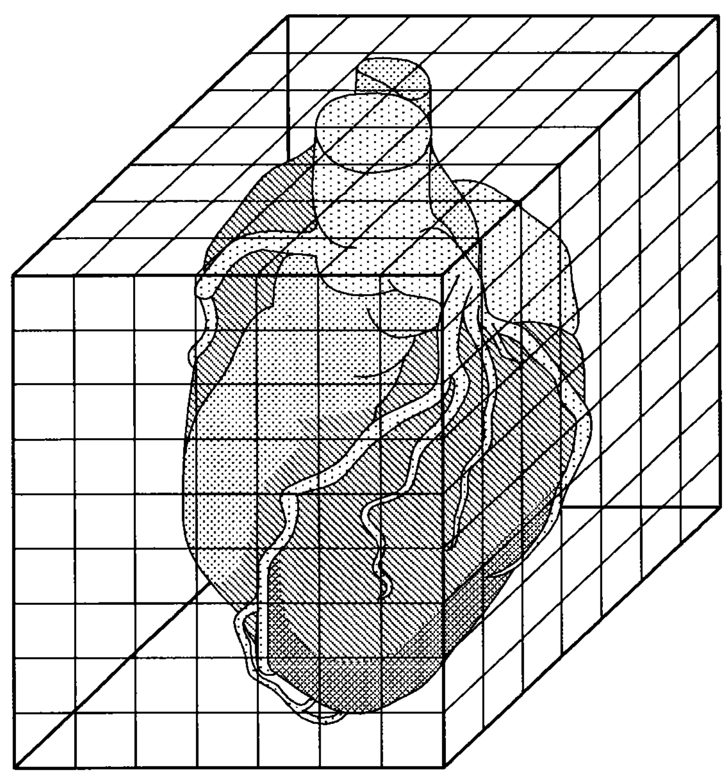

Here, the process of converting the scale in the stereoscopic image space into the scale in the volume data space may be applied to the case in which the grid line described with reference to FIG. 23 is used as the scale. In this case, the grid lines are displayed by straight lines or curved lines along the x direction, the y direction, and the z direction. When the scale in the volume data space using the grid line is used, the observer can easily discern a direction from which volume data is observed in the volume data space when observing the stereoscopic image through the stereoscopic display monitor without performing the process illustrated in FIG. 24C.

Regarding Scale Display

The third embodiment has been described in connection with the example in which the output unit 145*c* performs control such that the scale determined by the determining unit 145*b* is displayed. However, the scale may not be displayed according to the observer's desire. In other words, the output unit 145*c* performs control about whether to output the scale determined by the determining unit 145*b* according to the observer's request on the stereoscopic display monitor.

In other words, the observer may determine that the displayed scale is unnecessary when observing the stereoscopic image. In this case, for example, the operator of the terminal device 140 as the observer inputs a scale non-display request through the input unit 141. At this time, in order to cause the displayed scale to disappear, the output unit 145*c* converts a nine-parallax image on which the overlay of the scale is not superimposed into an interim image, and outputs the interim image to the display unit 142.

System Configuration

The third embodiment has been described in connection with the example in which the terminal device 140 acquires the correspondence information, determines the scale, and outputs the scale. However, in the third embodiment, the workstation 130 may acquire the correspondence information, determines the scale, and outputs the scale. In this case, the control unit 135 includes a processing unit corresponding to the acquiring unit 145*a*, a processing unit corresponding to the determining unit 145*b*, and a processing unit corresponding to the output unit 145*c*. The processing unit corresponding to the acquiring unit 145*a* acquires the correspondence information, and the processing unit corresponding to the determining unit 145*b* determines the scales in the X direction, the Y direction, and the Z direction based on the correspondence information.

Then, the processing unit corresponding to the output unit 145*c* performs control such that the nine-parallax image and the scale are output through the display unit 142. Specifically, through this process, the rendering processing unit 136 is controlled such that the overlay of the scale is generated, and then a 2D output image in which the generated overlay is superimposed on each of the underlays (the nine parallax images) is generated. Then, the processing unit corresponding to the output unit 145*c* controls the communication unit 133 such that nine 2D output images generated by the rendering processing unit 136 are transmitted to the terminal device 140 as the nine-parallax image. The communication unit 143 of the terminal device 140 transfers the received nine-parallax image to the control unit 145, and the control unit 145 converts the nine-parallax image into an interim image, and then outputs the interim image to the display unit 142. As a result, the display unit 142 displays the stereoscopic image together with the scale in the XYZ direction.

Further, the above embodiment has been described in connection with the example in which the workstation 130 generates the parallax image group. However, the parallax image group may be generated by the medical image diagnostic device 110. In this case, acquisition of the correspondence information, determination of the scale, and an output of the scale may be performed by the medical image diagnostic device 110. Further, the process related to "acquisition of the correspondence information, determination of the scale, and an output of the scale" described in the above embodiment may be performed only by the medical image diagnostic device 110, only by the workstation 130, or only by the terminal device 140. Further, the process related to "acquisition of the correspondence information, determination of the scale, and an output of the scale" described in the above embodiment may be performed between the medical image diagnostic device 110 and the workstation 130 or between the medical image diagnostic device 110 and the terminal device 140.

In other words, the process related to "acquisition of the correspondence information, determination of the scale, and an output of the scale" described in the above embodiment may be configured to be functionally or physically dispersed or integrated in arbitrary units according to various loads, or use conditions, or the like of the devices included in the image processing system 1. Further, all or any part of processing functions performed by the respective devices may be implemented by a CPU and a program analyzed and executed by the CPU or may be implemented as hardware by a wired logic.

As described above, according to the third embodiment, the scale to associate an image, stereoscopically viewed to the observer through the monitor with a stereoscopic view function, with the actual space can be displayed.

Further, among the processes described in the above embodiments, all or some of the processes described to be automatically performed may be manually performed. Alternatively, all or some of the processes described to be manually performed may be automatically performed by a well-known method. In addition, a process procedure, a control procedure, a concrete name, and information including various data or parameters which are described in this specification or illustrated in the drawings can be arbitrarily changed unless specified otherwise.

Further, each component of each device illustrated in the drawings is functionally conceptual, and needs not necessarily be physically configured as illustrated in the drawings. In other words, a specific form of dispersion or integration of respective devices is not limited to ones illustrated in the drawings, and all or some of respective devices may be functionally or physically dispersed or integrated in arbitrary units according to various loads, use conditions, or the like. For example, the control unit 135 of the workstation 130 may be connected via a network as an external device of the workstation 130.

Further, it is possible to create a program in which the process executed by the workstation 130 or the terminal device 140 in the above embodiments is described in a language executable by a computer. In this case, the same effects as in the above embodiments can be obtained by executing the program through the computer. Further, the program may be recorded in a computer readable recording medium, and the same process as in the above embodiment may be implemented by reading and executing the program recorded in the recording medium through the computer. For example, the program is recorded in a hard disk, a flexible disk (FD), a compact disc read only memory (CD-ROM), a magneto optical disc (MO), a digital versatile disc (DVD), a Blu-ray disc, or the like. Further, the program may be distributed via a network such as the Internet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system, comprising:

a stereoscopic display device; and an image processing apparatus, wherein the stereoscopic display device is configured to display a stereoscopically viewable stereoscopic image using a plurality of parallax images, and the image processing apparatus includes:

a transform circuit configured to generate transformed volume data from volume data, which is three-dimensional (3D) image data having a ratio of scale representing a scale in a depth direction with respect to a scale in other direction other than the depth direction, by reducing or enlarging at least one of the scale in the depth direction and the scale in the other direction within a range not exceeding a stereoscopic limit amount based on a scale in the depth direction of an assumed stereoscopic image assumed to be displayed on the stereoscopic display device using a parallax image group obtained by performing a rendering process on the volume data so as to maintain the ratio of scale in a stereoscopic image displayed on the stereoscopic display device using a parallax image group obtained by performing the rendering process on the transformed volume data, wherein the stereoscopic limit amount is an upper limit value of a size in a depth direction of the stereoscopically viewable stereoscopic image defined by specifications of the stereoscopic display device, an image generating circuit configured to generate a parallax image group by performing the rendering process on the transformed volume data, and a display control circuit configured to cause the parallax image group generated by the image generating circuit to be displayed on the stereoscopic display device.

2. The image processing system according to claim 1, further comprising:

a calculating circuit configured to calculate the stereoscopic limit amount, wherein the transform circuit reduces or enlarges the volume data in a range in which the size of the stereoscopic image, which is to be displayed on the stereoscopic display device, in the depth direction does not exceed the stereoscopic limit amount calculated by the calculating circuit.

3. The image processing system according to claim 2, wherein the transform circuit reduces or enlarges the volume data such that the size of the stereoscopic image, which is to be displayed on the stereoscopic display device, in the depth direction is substantially the same as the stereoscopic limit value calculated by the calculating circuit.

4. The image processing system according to claim 1, wherein the image generating circuit further generates a parallax image group by performing a rendering process on non-transformed volume data to be transformed by the transform circuit, and wherein the display control circuit causes the parallax image group generated from the transformed volume data by the image generating circuit and the parallax image group generated from the non-transformed volume data to be simultaneously displayed on the stereoscopic display device.

5. The image processing system according to claim 1, further comprising:

a correspondence information acquiring circuit configured to acquire correspondence information to associate space coordinates of a stereoscopic image to be stereoscopically viewed by referring to the stereoscopic display device that displays the parallax image group with space coordinates of a shooting portion of the volume data based on a display size of the parallax image group to be displayed on the stereoscopic display device, a determining circuit configured to determine a scale to convert a length in a vertical direction in a space of the stereoscopic image on the display surface of the stereoscopic display device into a length in a space of the shooting portion based on the correspondence information; and an output circuit configured to perform output control such that the scale on the stereoscopic image based on the parallax image group is displayed on the stereoscopic display device in a superimposed manner.

6. An image processing apparatus, comprising:

a stereoscopic display device configured to display a stereoscopically viewable stereoscopic image using a plurality of parallax images;

a transform circuit configured to generate transformed volume data from volume data which is three-dimensional (3D) image data having a ratio of scale representing a scale in a depth direction with respect to a scale in other direction other than the depth direction, by reducing or enlarging at least one of the scale in the depth direction and the scale in the other direction within a range not exceeding a stereoscopic limit amount based on a scale in the depth direction of an assumed stereoscopic image assumed to be displayed on the stereoscopic display device using a parallax image group obtained by performing a rendering process on the volume data so as to maintain the ratio of scale in a stereoscopic image displayed on the stereoscopic display device using a parallax image group obtained by performing the rendering process on the transformed volume data, wherein the stereoscopic limit amount is an upper limit value of a size in a depth direction of the stereoscopically viewable stereoscopic image defined by specifications of the stereoscopic display device;

an image generating circuit configured to generate a parallax image group by performing the rendering process on the transformed volume data; and a display control circuit configured to cause the parallax image group generated by the image generating circuit to be displayed on the stereoscopic display device.

7. An image processing method executed by an image processing system including a stereoscopic display device that displays a stereoscopically viewable stereoscopic image using a plurality of parallax images, the method comprising:

generating transformed volume data from volume data which is three-dimensional (3D) image data having a ratio of scale representing a scale in a depth direction with respect to a scale in other direction other than the depth direction, by reducing or enlarging at least one of the scale in the depth direction and the scale in the other direction within a range not exceeding a stereoscopic limit amount based on a scale in the depth direction of an assumed stereoscopic image assumed to be displayed on the stereoscopic display device using a parallax image group obtained by performing a rendering process on the volume data so as to maintain the ratio of scale in a stereoscopic image displayed on the stereoscopic display device using a parallax image group obtained by performing the rendering process on the transformed volume data, wherein the stereoscopic limit amount is an upper limit value of a size in a depth direction of the stereoscopically viewable stereoscopic image defined by specifications of the stereoscopic display device;

generating a parallax image group by performing the rendering process on the transformed volume data; and causing the generated parallax image group to be displayed on the stereoscopic display device.

* * * * *